(12) United States Patent
Bazan et al.

(10) Patent No.: US 8,841,072 B2
(45) Date of Patent: *Sep. 23, 2014

(54) METHODS AND COMPOSITIONS FOR DETECTION AND ANALYSIS OF POLYNUCLEOTIDES USING LIGHT HARVESTING MULTICHROMOPHORES

(71) Applicant: The Regents of the University of California, Oakland, CA (US)

(72) Inventors: Guillermo C. Bazan, Santa Barbara, CA (US); Brent S. Gaylord, San Diego, CA (US); Shu Wang, Beijing (CN)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/086,532

(22) Filed: Nov. 21, 2013

(65) Prior Publication Data

US 2014/0141428 A1    May 22, 2014

Related U.S. Application Data

(60) Continuation of application No. 13/544,303, filed on Jul. 9, 2012, now Pat. No. 8,617,814, which is a continuation of application No. 12/632,734, filed on Dec. 7, 2009, now Pat. No. 8,227,187, which is a continuation of application No. 11/854,365, filed on Sep. 12, 2007, now Pat. No. 7,629,448, which is a division of application No. 10/648,945, filed on Aug. 26, 2003, now Pat. No. 7,270,956.

(60) Provisional application No. 60/406,266, filed on Aug. 26, 2002.

(51) Int. Cl.
*C12Q 1/68*     (2006.01)
*C07H 19/04*   (2006.01)

(52) U.S. Cl.
USPC .................. 435/6.1; 536/23.1; 536/26.6

(58) Field of Classification Search
USPC ................. 435/6.1; 536/23.1, 26.6
See application file for complete search history.

(56) References Cited

U.S. PATENT DOCUMENTS

| | | | |
|---|---|---|---|
| 4,948,843 | A | 8/1990 | Roberts et al. |
| 4,950,587 | A | 8/1990 | Roberts et al. |

(Continued)

FOREIGN PATENT DOCUMENTS

| | | |
|---|---|---|
| EP | 0708837 | 5/1996 |
| EP | 1281744 | 2/2003 |

(Continued)

OTHER PUBLICATIONS

Ajayaghosh, et at., "A novel approach toward low optical band gap polysquaraines", Organic Letters, 3(16):2595-2598, 2001.

(Continued)

*Primary Examiner* — Jezia Riley
(74) *Attorney, Agent, or Firm* — Glenn J. Foulds; Bret E. Field; Bozicevic, Field & Francis, LLP

(57) ABSTRACT

Methods, compositions and articles of manufacture for assaying a sample for a target polynucleotide are provided. A sample suspected of containing the target polynucleotide is contacted with a polycationic multichromophore and a sensor polynucleotide complementary to the target polynucleotide. The sensor polynucleotide comprises a signaling chromophore to receive energy from the excited multichromophore and increase emission in the presence of the target polynucleotide. The methods can be used in multiplex form. Kits comprising reagents for performing such methods are also provided.

12 Claims, 5 Drawing Sheets

(56) References Cited

U.S. PATENT DOCUMENTS

| | | | |
|---|---|---|---|
| 5,408,109 | A | 4/1995 | Heeger et al. |
| 5,612,221 | A | 3/1997 | Simons et al. |
| 5,869,350 | A | 2/1999 | Heeger et al. |
| 5,881,083 | A | 3/1999 | Diaz-Garcia et al. |
| 5,968,762 | A | 10/1999 | Jadamec et al. |
| 5,990,479 | A | 11/1999 | Weiss et al. |
| 6,090,552 | A | 7/2000 | Nazarenko et al. |
| 6,263,286 | B1 | 7/2001 | Gilmanshin et al. |
| 6,280,933 | B1 | 8/2001 | Glazer et al. |
| 6,350,431 | B1 | 2/2002 | Snow et al. |
| 6,534,329 | B2 | 3/2003 | Heeger et al. |
| 6,545,164 | B1 | 4/2003 | Waggoner et al. |
| 6,579,726 | B1 | 6/2003 | Natan et al. |
| 6,589,731 | B1 | 7/2003 | Chen et al. |
| 6,743,640 | B2 | 6/2004 | Whitten et al. |
| 6,808,542 | B2 | 10/2004 | Nguyen et al. |
| 6,951,682 | B1 | 10/2005 | Zebala |
| 6,979,543 | B2 | 12/2005 | Chen et al. |
| 7,122,383 | B2 | 10/2006 | Jones et al. |
| 7,141,437 | B2 | 11/2006 | Dvornic et al. |
| 7,208,122 | B2 | 4/2007 | Swager et al. |
| 7,214,489 | B2 | 5/2007 | Bazan et al. |
| 7,270,956 | B2 | 9/2007 | Bazan et al. |
| 7,629,448 | B2 | 12/2009 | Bazan et al. |
| 2001/0026921 | A1 | 10/2001 | Rabbani et al. |
| 2002/0009728 | A1 | 1/2002 | Bittner et al. |
| 2002/0034747 | A1 | 3/2002 | Bruchez, Jr. et al. |
| 2002/0150759 | A1 | 10/2002 | Jones et al. |
| 2002/0177136 | A1 | 11/2002 | McBranch et al. |
| 2003/0054413 | A1 | 3/2003 | Kumaraswamy et al. |
| 2003/0087311 | A1 | 5/2003 | Wolf |
| 2004/0009506 | A1 | 1/2004 | Stephan et al. |
| 2004/0023248 | A1 | 2/2004 | O'Malley |
| 2004/0023317 | A1 | 2/2004 | Motamedi et al. |
| 2004/0241768 | A1 | 12/2004 | Whitten et al. |
| 2005/0064239 | A1 | 3/2005 | Take |
| 2005/0064604 | A1 | 3/2005 | Bohmann et al. |
| 2005/0196775 | A1 | 9/2005 | Swager et al. |
| 2006/0073607 | A1 | 4/2006 | Rose et al. |
| 2006/0127929 | A1 | 6/2006 | Swager et al. |
| 2006/0175193 | A1 | 8/2006 | Inganas et al. |
| 2006/0216759 | A1 | 9/2006 | Naasani |
| 2007/0178470 | A1 | 8/2007 | Bissonnette et al. |
| 2008/0038751 | A1 | 2/2008 | Asberg et al. |

FOREIGN PATENT DOCUMENTS

| | | |
|---|---|---|
| EP | 0990903 | 3/2003 |
| EP | 0684239 | 12/2003 |
| EP | 1279023 | 9/2004 |
| WO | WO9935288 | 7/1999 |
| WO | WO0014278 | 3/2000 |
| WO | WO0066790 | 11/2000 |
| WO | WO0101144 | 1/2001 |
| WO | WO0195059 | 12/2001 |
| WO | WO02081735 | 10/2002 |
| WO | WO02084271 | 10/2002 |
| WO | WO04001379 | 12/2003 |
| WO | WO2004037886 | 5/2004 |
| WO | WO2004077014 | 9/2004 |
| WO | WO2006092063 | 9/2006 |
| WO | WO2007001438 | 1/2007 |

OTHER PUBLICATIONS

Balakin et al., "Conjugates of oligonucleotides with polyaromatic fluorophores as promising DNA probes", Biosensors & Bioelectronics, 1998, 13, 771-778.

Bardea, et al., "Sensing and amplification of oligonucleotide-DNA interactions by means of impedance spectroscopy: a route to a Tay-Sachs sensor", Chem. Commun., 1999, 21-22.

Baur, et al., "Thin-Film Light-Emitting Devices Based on Sequentially Adsorbed Multilayers of Water-Soluble Poly (p-phenylene)s", Advanced Materials (1998) 10:17:1452-1455.

Bazan,"Characterisation of tectoRNA Assembly with cationic conjugated polymers", JACS, 126(13):4076-7044, 2004.

Behr, J.P. Synthetic Gene-Transfer Vectors; Ace. Chem. Res.,1993, 26: 274-278.

Behr, J.P. DNA Strongly Binds to Micelles and Vesicles Containing Lipopolyamines or Lipointercalants: Tetrahedron Lett. (1986) 27:48:5861-5864.

Beier, et al., "Versatile derivatisation of solid support media for covalent bonding on DNA-microchips", Nucleic Acids Research, 1999, 27(9), 1970-1977.

Benson, S.C. et al. Heterodimeric DNA-binding dyes designed for energy transfer: synthesis and spectroscopic properties; Nucleic Acids Res. (1993) 21:24:5727-5735.

Betts, et al. A Nucleic Acid Triple Helix Formed by a Peptide Nucleic Acid-DNA Complex; Science, 1995, 270:1838-1841.

Bhattacharya, et al., "Interaction of surfactants with DNA. Role of hydrophobicity and surface charge on intercalation and DNA melting", Biochim.et Biophys. Acta. (1997) 1323:29-44.

Bhattacharya, et al., "Role of hydrophobic effect and surface charge in surfactant-DNA association", Indian J. Biochem. & Biophys. (1997) 34:11-17.

Bier, et at., "Feature-size limitations of microarray technology—a critical review", Fresenius J. Anal. Chem., 2001, 371:151-156.

Birnboim, et al., "Fluorometric Method for Rapid Detection of DNA Strand Breaks in Human White Blood Cells Produced by Low Doses of Radiation", Cancer Res.,1981, 41:1889-1892.

Blessing, et al., "Monomolecular collapse of plasmid DNA into stable virus-like particles", Proc. Nat/. Acad. Sci.USA, 1998, 95:1427-1431.

Brandt, et al., "Peptide nucleic acids on microarrays and other biosensors," TIBS, 22(12):617-622, 2004.

Bronich, et al., "Recognition of DNA Topology in Reactions between Plasmid DNA and Cationic Copolymers", J. Am. Chern. Soc., Sep. 2000, 122(35), 8339-8343.

Cardullo, et al., "Detection of Nucleic Acid Hybridization by Non radiative Fluorescence Resonance Energy Transfer", Proc. Natl. Acad. Sci. USA, Dec. 1998, 85, 8790-8794.

Castro, et al.,"Single-molecule detection of specific nucleic acid sequences in unamplified genomic DNA", Anal. Chem. (1997) 69:19:3915-3920.

Chandar, et al. "Fluorescence probe investigation of anionic polymer-cationic surfactant interactions", Macromolecules (1988) 21:950-953.

Chehab, et al., "Detection of specific DNA sequences by flu9rescence amplification: A color complementation assay",Proc. Nat/. Acad. Sci. USA (1989) 86:9178-9182.

Chen, et al., "A peptide interaction in the major groove of RNA resembles protein interactions in the minor groove of DNA", Proc. Nat/. Acad. Sci. USA. (1995) 92:5077-5081.

Chen, et al., "Highly sensitive biological and chemical sensors based on reversible fluorescence quenching in a conjugated polymer" Proc. Nat/. Acad. Sci. USA. (1999) 96:22:12287-12292.

Chen, et al. "Using Ethidium Bromide to Probe the Interactions between DNA and Dendrimers", Langmuir (2000) 16:15-19.

Chen, et al. "Highly sensitive biological and chemical sensors based on reversible fluorescence quenching in a conjugated polymer", PNAS, 1999, 96(22), 12287-12292.

Chen, et al. "Tuning the Properties of Conjugated Polyelectrolytes through Surfactant Complexation", J. Am. Chern. Soc., 2000, 122, 9302-9303.

Delling, et al. "The number of positively charged amino acids in the basic domain of Tat is critical for transactivation and complex formation with TAR RNA", Proc. Nat/. Acad. Sci. USA (1991) 88:6234-6238.

Demers, et al., "Thermal desorption behavior and binding properties of DNA bases and nucleosides on gold", J Am Chem Soc. 2002;124(38):11248-9.

Demidov, "PNA and LNA throw light on DNA", Trends in Biotechnology (2003) 21:1:4-7.

Demidov, et al. "Stability of peptide nucleic acids in human serum and cellular extracts", Biochem. Phaimacol. (1994) 48:6:1310-1313.

De Smedt, et al. "Cationic Polymer Based Gene Delivery Systems" Pharm. Res. (2000) 17:2:113-126.

(56) References Cited

OTHER PUBLICATIONS

Didenko, "DNA Probes Using Fluorescence Resonance Energy Transfer (FRET): Designs and Applications", *Bio Techniques* (2001) 31:5:1106-1121.
Dogariu, et al. Time-resolved Forster energy transfer in polymer blends; *Synthetic Metals* (1999) 100:95-100.
Dore, et al., "Fluorescent Polymeric Transducer for the Rapid, Simple, and Specific Detection of Nucleic Acids at the Zeptomole Level", J. Am. Chem. Soc., 2004, 126, 4240-4244.
Dufourcq, et al. "Molecular assembling of DNA with amphipathic peptides", *FEBS Lett.* (1998) 421:7-11.
Eastman, et al. Biophysical characterization of cationic lipid: DNA complexes; *Biochim. et Biophys. Acta* (1997) 1325:41-62.
Epstein, et al., "Microarray technology—enhanced versatility, persistent challenge", Current Opinion in Biotechnology, 2000, 11, 36-41.
Egholm, et al. "PNA hybridizes to complementary oligonucleotides obeying the Watson-Crick hydrogenbonding Rules", *Nature* (1993) 365:566-568.
Egholm, et al. "Recognition of Guanine and Adenine in DNA by Cytosine and Thymine Containing Peptide Nucleic Acids (PNA)", *J. Am. Chem.* Soc. (1992) 114:9677-9678.
Englebienne, P. Synthetic materials capable of reporting biomolecular recognition events by chromic transition; *J. Mater Chem.* (1999) 9:1043-1054.
Eskilsson, et al. "DNA-Surfactant Complexes at Solid Surfaces", Langmuir (2001) 17:1666-1669.
Felgner, et al. "Nomenclature for Synthetic Gene Delivery Systems", *Hum. Gene Ther.* (1997) 8:511-512.
Ferguson, et al., "Localization of Noncovalently Bound Ethidium in Free and Methionyl-tRNA Synthetase Bound tRNAfMet by Singlet-Singlet Energy Transfer", *Biochemistry* (1986) 25:5298-5304.
Fernandez-Saiz et al. "A Cationic Cyclophane That Forms a Base-Pair Open Complex with RNA Duplexes", *J. Am. Chern. Soc.* (1996) 118:4739-4745.
Frankel,"Peptide models of the Tat-TAR protein-RNA interaction", *Prot. Sci.* (1992) 1:1539-1542.
Futami, et al. "Optimum Modification for the Highest Cytotoxicity of Cationized Ribonuclease", *J. Biochem.* (2002) 132:223-228.
Gallego, et al., "Targeting RNA with Small-Molecule Drugs: Therapeutic Promise and Chemical Challenges" *Acc. Chem. Res.* (2001) 34:10:836-843.
Gallo, et al., "AIDS in 1988", *Sci. Am.* (1988) 259:4:41-48.
Ganachaud, et al. "Adsorption of Single-Stranded DNA Fragments onto Cationic Aminated Latex Particles", *Langmuir*(1997) 13:701-707.
Gallot, et al., "Poly(L-lysine) containing azobenzene units in the side chains: influence of the degree of substitution on liquid crystalline structure and thermotropic behaviour", Liquid Crystals, 1997, 23(1), 137-146.
Gaylord, "SNP detection using peptide nucleic acid probes and conjugated polymers: Applications in neurodegenerative disease identification", PNAS, 102(1):34-39, 2005.
Gaylord, et al., "Water-Soluble Conjugated Oligomers: Effect of Chain Length and Aggregation on Photoluminescence-Quenching Efficiencies", J. Am. Chem. Soc., 2001, 123, 6417-6418.
Gaylord, et al., "DNA Hybridization Detection with Water-Soluble Conjugated Polymers and Chromophore-Labeled Single-Stranded DNA", J. Am. Chem. Soc., 2003, 125, 896-900.
Gaylord, "DNA detection using water-soluble conjugated polymers and peptide nucleic acid probes", PNAS, 99(17):182, 2002.
Gershon, et al. "Mode of Formation and Structural Features of DNA-Cationic L_iposome Complexes Used for Transfection", *Biochemistry* { 1993) 32:7143-7151.
Giesen, et al. "A formula for thermal stability {Tm) prediction of PNA!DNA duplexes", *Nucleic Acids* Res. {1998) 26:21 :5004-5006.
Gossl, et al. "Molecular Structure of Single DNA Complexes with Positively Charged Dendronized Polymers", *J.Am. Chem.* Soc. {2002) 124:6860-6865.
Hage, "Immunoassays", *Anal. Chem.* {1999) 71:12:294R-304R.

Hanvey, et al. "Antisense and Antigene Properties of Peptide Nucleic Acids", *Science* {1992) 258:1481-1485.
Harada, et al., "Chain Length Recognition: Core-Shell Supramolecular Assembly from Oppositely Charged Block Copolymers", *Science* {1999) 283:65-67.
Hawkins, et al., "Incorporation of a fluorescent guanosine analog into oligonucleotides and its application to a real time assay for the HIV-1 integrase 3'-processing reaction", Nucleic Acids Research, 1995, 23(15),2872-2880.
Heeger, et al., "Making Sense of polymer-based biosensors", PNAS, Oct. 1999, 96(22), 12219-12221.
Ho, et al., "Colorimetric and Fluormetric Detection of Nucleic Acids Using Cationic Polythiophene Derivatives", Angew. Chem. Int. Ed., 2002, 41(9), 1548-1551.
Hong, et al., "Water-Soluble Oligmer Dimers Based on Paracyclophane: A New optical Platform for Fluorescent Sensor Applications", J. Am. Chem. Soc., 2002, 124, 11868-11869.
Huang, et al., "High-Efficiency, Evironment-Friendly Electroluminescent Polymers with Stable High Work Function Metal as a Cathode: Green- and Yellow-Emitting Conjugated Polyfluorene Polyelectrolytes and Their Neutral Precursors", J. Am. Chem. Soc., 2004, 126, 9845-9853.
Huang, "Novel Electroluminescent Conjugated Polyelectrolytes based on Polyfluorene", Chemistry of Materials, Am., Chem. Soc., 16(4):708-716, 2004.
Isola, et al. "Surface-Enhanced Raman Gene Probe for HIV Detection", *Anal. Chem.* (1998) 70:1352-1356.
Izumrudov, et al. "The influence of chain length of a competitive polyanion and nature of monovalent counterions on the direction of the substitution reaction of polyelectrolyte complexes", *Makromol. Chem., Rapid Commun.* { 1988) 9:7-12.
Izumrudov, et al. "Competitive Reactions in Solutions of DNA and Water-Soluble Interpolyelectrolyte Complexes" *Biopolymers* (1995) 35:523-531.
Izumrudov, et al. "Competitive Displacement of Ethidium Cations Intercalated in DNA by Polycations", *Dokl. Phys. Chern.* {1995) 342:Nos. 4-6: 150-153.
Izumrudov, et al. "Ethidium Bromide as a Promising Probe for Studying DNA Interaction with Cationic Amphiphiles and Stability of the Resulting Complexes", *Langmuir* {2002) 18:10348-10356.
Izumrudov, et al. "Controllable Stability of DNA-Containing Polyelectrolyte Complexes in Water-Salt Solutions", *Biopolymers.* {1999) 52:94-108.
Izumrudov, et al., "Stability of DNA-containing interpolyelectrolyte complexes in watersalt Solutions", *Macromol. Chem. Phys.* {1999) 200:11 :2533-2540.
Jain, et al., "Rapid Genetic Analysis of RNA-Protein Interactions by Translational Repression in *Escherichia coli*", *Methods Enzymol.* {2000) 318:309-332.
Jenkins, et al. "A Sequence-Specific Molecular Light Switch: Tethering of an Oligonucleotide to a Dipyridophenazine Complex of Ruthenium (II)", *J. Am. Chem. Soc.* (1992) 114:8736-8738.
Johansson, et al. "Intramolecular Dimers: A New Strategy to Fluorescence Quenching in Dual-Labeled Oligonucleotide Probes", *J. Am. Chem. Soc.* (2002) 124:6950-6956.
Junhui, et al. "DNA Based Biosensors", *Biotechnol. Adv.* (1997) 15:43-58.
Kabanov, et al. "DNA Interpolyelectrolyte Complexes as a Tool for Efficient Cell Transformation", *Biopolymers.* (1991) 31:1437-1443.
Kabanov, et al., "DNA Complexes with Polycations for the Delivery of Genetic Material into Cells", *Bioconjugate Chem.* (1995) 6:7-20.
Kabanov, et al. "Cooperative Interpolyelectrolyte Reactions", *Makromol. Chem. Suppl.* (1985) 13:137-155.
Karn, et al. "HIV a Practical Approach; RNA binding assays for the regulatory proteins Tat and Rev" *IRL Press*,New York; (1995) 9:147-165.
Katayose, et al., "Water-Soluble Polyion Complex Associates of DNA and Poly(ethylene glycol)-Poly(L-lysine) Block Copolymer", *Bioconjugate Chem.* (1997) 8:702-707.
Kircheis, et al. "Tumor targeting with surface-shielded ligand-polycation DNA complexes", *J. Controlled Release*; (2001) 72:165-170.

(56) References Cited

OTHER PUBLICATIONS

Kirsh, et al. "Comparison of Properties of an Oxime-Bound Partially Quaternized Poly-4-Vinylpyridine and a Monomer Analogous Oxime", *Eur. Polym. J.* (1974) 10:393-399.

Knemeyer, et al, "Probes for detection of specific DNA", Anal. Chem, 72:3717-3724, 2000.

Kwon, et al. "Electrically Erodible polymer gel for controlled release of drugs", *Nature* (1991) 354:291-293.

Leclerc, "Optical and Electrochemical Transducers Based on Functionalized Conjugated Polymers", Adv. Mater., 1999, 11(18), 1491-1498.

Lee, et al. "ResonSense®: simple linear fluorescent probes for quantitative homogeneous rapid polymerase chain reaction", *Anal. Chim. Acta* (2002) 457:61-70.

Le-Pecq, et al., "A Fluorescent Complex between Ethidium Bromide and Nucleic Acids", *J. Mol Bioi.* (1967) 27:87-106.

Leulliot, et al., "Current Topics in RNA-Protein Recognition: Control of Specificity and Biological Function through Induced Fit and Conformational Capture", *Biochemistry* (2001) 40:27:7947-7956.

Lipshutz et al., "High density synthetic oligonucleotide arrays", Nature Genetics Supplement, Jan. 1999, 21, 20-24.

Liu et al., "Blue-light -emitting cationic water-soluble polyfluorene derivatives with tunable quaternization degree", Macromolecules, 35(13):4975-4982, 2002.

Liu, et al., "Homogeneuos Fluorescents-Based DNA Detection with Water-Soluble Conjugated Polymers", Chern. Mater., 2004, 16, 4467-4476.

Liu, et al., "Effect of Chromophore-Charge Distance in the Energy Transfer Properties of Water-Soluble Conjugated Oligomers", J. Am. Chern. Soc., 2003, 125, 6705-6714.

Liu, et al., "Methods for strand-specific DNA detection with cationic conjugation polymers suitable for incorporation into DNA chips and microarrays", PNAS Early Edition, 2004, p. 1-5.

Liu, et al., "Shape-Adapable Water-Soluble Conjugated Polymers", J. Am. Cham. Soc., 2003, 125, 13306-13307.

Liu, et al., "Interpolyelectrolyte Complexes of Conjugated Copolymers and DNA: Platforms for Multicolor Biosensors", J. Am. Chern. Soc., 2004, 126, 1942-1943.

Lohse, et al., "Fluorescein-Conjugated Lysine Monomers for Solid Phase Synthesis of Fluorescents Peptides and PNA Oligomers", Bioconjugate Chern., 1997, 8, 503-509.

Makino, et al. "Molecular Characterization and Protein Analysis of the *cap* Region, Which is Essential for Encapsulation in *Bacillus anthracis*" *J. Bacteriol.* (1989) 171:2:722-730.

Manning, G.S. "Thermodynamic Stability Theory for DNA Doughnut Shapes Induced by Charge Neutralization" *Biopolymers.* (1980) 19:37-59.

Manning, G.S. "The Possibility of Intrinsic Local Curvature in DNA Toroids", *Biopolymers.* (1981) 20:1261-1270.

Manning, G.S. "The molecular theory of polyelectrolyte solutions with applications to the electrostatic properties of polynucleotides" *Qrtly Review of Biophysics.* (1978) v.11: 179-246.

Maruyama et al. "Characterization of Interpolyelectrolyte Complexes between Double-Stranded DNA and Polylysine Comb-Type Copolymers Having Hydrophilic Side Chains", *Bioconjugate Chern.* (1998) 9:292-299.

Matsumoto, et al. "High-Throughput Screening Utilizing Intramolecular Fluorescence Resonance Energy Transfer for the Discovery of the Molecules that Bind HIV-1 TAR RNA Specifically", *Bioorg. Med. Chern. Lett.* (2000)10:1857-1861.

McLoughlin, et al. "A simple and effective separation and purification procedure for DNA fragments using Dodecyltrimethylammonium bromide", *Bioseparation.* (2001) 9:307-313.

McQuade, et al., "Conjugated Polymer-Based Chemical Sensors", Chem. Rev., 2000, 100, 2537-2574.

McQuade, et al. "Signal amplification of a "Tum-On" Sensor: Harvesting the Light Captured by a Conjugated Polymer", *J. Am. Chern. Soc.* (2000) 122:12389-12390.

Mel'Nikov, et al. "Discrete Coil -Globule Transition of Large DNA Induced by Cationic Surfactant", *J. Am. Chern. Soc.* (1995) 117:2401-2408.

Mergny, et al. "Fluorescence Energy Transfer between Two Triple Helix-Forming Oligonucleotides Bound to Duplex DNA" *Biochemistry.* (1994) 33:15321-15328.

Miao, et al. "Photophysics of Poly(paracyclophan-1-ene) and Derivatives: Evidence for Intrachain Energy Transfer and Chromophore Aggregation", *J. Am. Chern. Soc.* (1995) 117:11407-11420.

Miller, I.R. "Interaction of DNA with Heavy Metal Ions and Polybases: Cooperative Phenomena", *Biopolymers.* (1968) 6:169-179.

Minehan, et al. "Kinetics of DNA Binding to Electrically Conducting Polypyrrole Films", *Macromolecules.* (1994) 27:777-783.

Morgan, et al., "Native and Denatured DNA, Cross-Linked and Palindromic DNA and Circular CovalenUy-Ciosed DNA Analysed by a Sensitive Fluorometric Procedure", *Biochem. Biophys. Res. Commun.* (1974) 61:2:396-403.

Nilsson, et al., "Chip solution detection of DNA hybridization using a luminescent zwitterionic polythiophene derivative", Nature Materials, Jun. 2003, 2, 419-424 (Supplementary Information pp. 1-2).

Nielsen, P.E. "Applications of peptide nucleic acids", *Analytical biotechnology.* (1999) 10:71-75.

Nguyen, et al. "Nonviral Transfer Technology: Evaluation of polyether-polyethyleneimine graft copolymers as gene transfer agents", *Gene Ther.* (2000) 7:126-138.

Nishanian, et al. "A Simple Method for Improved Assay Demonstrates that HIV p24 Antigen is Present as Immune Complexes in Most Sera from HIV-Infected Individuals", *J. Infect. Dis.* (1990) 162:21-28.

Nuovo, G.J. "In Situ Localization of PCR-Amplified DNA and eDNA", *Methods Mol. Bio.* (2000) 123:217-238.

Olins, et al. "Model Nucleoprotein Complexes: Studies on the Interaction of Cationic Homopolypeptides with DNA" *J. Mol. Bioi.* (1967) 24:157-176.

Pasternack, et al. "Long-Range Fluorescence Quenching of Ethidium Ion by Cationic Porphyrins in the Presence of DNA", *J. Am. Chem. Soc.* (1991) 113:6835-6840.

Patel, et al., "Energy transfer analysis of Fos-Jun dimerization and DNA binding", Proc. Natl. Sci. USA, Jul. 1994, 91, 7360-7364.

Patolsky, et al. "Amplified DNA Detection by Electrogenerated Biochemiluminescence and by the Catalyzed Precipitation of an Insoluble Product on Electrodes in the Presence of the Doxorubicin Intercalator", *Angew. Chem. Int. Ed.* (2002) 41:18:3398-3402.

Patolsky, et al. "Electronic Transduction of DNA Sensing Processes on Surfaces: Amplification of DNA Detection and Analysis of Single-Base Mismatches by Tagged Liposomes", *J. Am Chem. Soc.* (2001) 123:5194-5205.

Peterlinz, et al. "Observation of Hybridization and Dehybridization of Thioi-Tethered DNA using Two-Color Surface Plasmon Resonance Spectroscopy", *J. Am. Chem. Soc.* (1997} 119:3401-3402.

Petty, et al. "Thermodynamic Characterization of the Association of Cyanine Dyes with DNA", *J. Phys. Chern. B.* (2000} 104:7221-7227.

Pilipenko, et al. "A cell cyde-dependent protein serves as a template-specific translation initiation factor", *Genes & Dev.* (:2000} 14:2028•2045.

Pinto, et al., "Conjugated Polyelectrolytes: Synthesis and Applications", *Synthesis.* (2002) 9:1293-1309.

Plank, et al. "Branched Cationic Peptides for Gene Delivery: Role of Type and Number of Cationic Residues in Formation and in Vitro Activity of DNA Polyplexes", *Hum. Gene Ther.* (1999} 10:319-332.

Portela, et al., "The influenza virus nucleoprotein: a multifunctional RNA-binding protein pivotal to virus replication", *J. Gen. Virol.* (2002} 83:723-734.

Puglisi, et al. "Conformation of the TAR RNA-Arginine Complex by NMR Spectroscopy", *Science.* (1992) 257:76-80.

Pullman, et al. "Two Aspects of DNA Polymorphism and Microheterogeneity: Molecular Electrostatic Potential and Steric Accesibility", *J. Biochem.* (1982} 124:229-238.

Raymond, "Detection of target DNA using fluoresence cationic polymer and peptide nucleic acid probes on solid support", BMD Biotechnology, vol. 5, 2005.

(56) References Cited

OTHER PUBLICATIONS

Ranade, et al., "High-Throughput Genotyping with Single Nucleotide Polymorphisms", Genone Research, 2001, 11, 1262-1268.
Richter, et al. "Specific HIV-1 TAR RNA Loop Sequence and Functional Groups are Required for Human Cyclin T1-Tat-TAR Ternary Complex Formation", *Biochemistry.* (2002) 41:6391-6397.
Saghatelian, et al. "DNA Detection and Signal Amplification via an Engineered Allosteric Enzyme", *J. Am. Chern. Soc.* (2003) 125:344-345.
Saiki, et al. "Enzymatic Amplification of ~-Globin Genomic Sequences and Restriction Site Analysis for Diagnosis of Sickle Cell Enemia", *Science.* (1985) 230:1350-1354.
Seymour, et al. "Cationic block copolymers as self-assembling vectors for gene delivery; *Self-assembling Complexes for Gene Delivery*", (1998) 11:219-239.
Shinozuka, et al. "A Novel MuiUfunctionalily Labelled DNA Probe Bearing an Intercalator and a Fluorophore", *J.Chem. Soc., Chern. Commun.* (1994) 1377-1378.
Schork, et al., "Single nucleotide polymorphisms and the future of genetic epidemiology", Clin. Genet., 2000, 58, 250-264.
Service "DNA Analysis: Microchip Arrays Put DNA on the Spot", The American Association for the Advancement of Science, Oct. 1998, 282(5388), 396-399.
Smith, et al., "The synthesis of oligonucleotides containing an aliphatic amino group at the 5' terminus: synthesis of fluorescent DNA primers for use in DNA sequence analysis", Nucleic Acids Research, 1985, 13(7) 2399-2412.
Smith, et al. "Molecular Recognition of PNA-Containing Hybrids: Spontaneous Assembly of Helical Cyanine Dye Aggregates on PNA Templates", *J. Ant Chern. Soc.* (1999) 121:2686-2695.
Smith, et al. "Surfactant structure around DNA in aqueous solution", *Phys. Chern. Chem. Phys.* (2000) 2:1305-1310.
Southern, "DNA chips: analysing sequence by hybridization to oligonucleotides on a large scale", TIG, Mar. 1996, 12(3), 110-115.
Stender, et al. "PNA for rapid microbiology", *J. Microbiological Methods.* (2002) 48:1-17.
Stork, et al. "Energy Transfer in Mixtures of Water-Soluble Oligomers: Effect of Charge, Aggregation, and Surfactant Complexation", *Adv. Mater.* (2002) 14:5:361-366.
Stewart, "Chromophore-Labeled Dendrons as Light Harvesting Antennae", J. Am. Chern. Soc., 118 (18):4354-4360, 1996.
Stevens, et al., "Exciton dissociation mechanisms in the polymeric semiconductors poly(9,9-dioctylfluorene) and poly(9,9-dioctylfluorene-co-benzothiadiazole)", Physical Review 8, Apr. 2001, 63, 1-18.
Stork, et al. "Energy Transfer in Mixtures of Water-Soluble Oligomers: Effect of Charge, Aggregation, and Surfactant Complexation", Adv. Mater., Mar. 2002, 14(5), 361-366.
Su, et al. "Au nanoparticle- and silver-enhancement reaction-amplified microgravimetric biosensor",*Chem. Commun.* (2001) 755-756.
Sullenger, et al., "Emerging clinical applications of RNA", *Nature.* (2002) 418:252-258.
Sun et al., "Application of cationic conjugated polymers in microarrays using label-free DNA targets," Nature Protocols, 2(9):2007.
Takakusa, et al. "Design and Synthesis of an Enzyme-Cleavable Sensor Molecule Jor Phosphodiesterase Activity Based on Fluorescence Resonance Energy Transfer", *J. Am. Chern. Soc.* (2002) 124:8:1653-1657.
Tamilarasu, et al. "A New Strategy for Site-Specific Protein Modification: Analysis of a Tat Peptide-TAR RNA Interaction", *Bioconjugate Chern.* (2001) 12:2:135-138.
Tang, et al., "The influence of polymer structure on the interactions of cationic polymers with DNA and morphology of the resulting complexes" *Gene Ther.* (1997) 4:823-832.
Taton, et al. "Scanometric DNA Array Detection with Nanoparticle Probes", *Science.* (2000) 289:1757-1760.
Taton, et al. "Two-Color Labeling of Oligonucleotide Arrays via Size-Selective Scattering of Nanoparticle Probes", *J. Am. Chem. Soc.* (2001) 123:5164-5165.
Tomac, et al. "Ionic Effects on the Stability and Conformation of Peptide Nucleic Acid Complexes", *J. Am. Chem.Soc.* (1996) 118:5544-5552.
Traser, et al. "Syntheses and solution properties of water-soluble poly(p-phenylene)s bearing oligo( ethylene oxide) and trialkylamino side groups", *e-Polymers.* (2002) 32:1-39.
Umek, et al., "Electronic Detection of Nucleic Acids, A Versatile Platform for Molecular Diagnostics", Journal of Molecular Diagnostics, May 2001, 3(2), 74-84.
Vehese, et al., "Light Amplification by Optical Excitation of a Chemical Defect in a Conjugated Polymer", Adv. Mater., Jun. 2004, 16(12), 1001-1004.
Vaishnav, et al. "The Biochemistry of Aids", *Ann. Rev. Biochem.* (1991) 60:577-630.
Varani, G. "RNA-Protein Intermolecular Recognition" *Ace. Chem. Res.* (1997) 30:5:189-195.
Vinogradov,et al. "Self-Assembly of Polyamine-Poly( ethylene glycol) Copolymers with Phosphorothioate Oligonucleotides", *Bioconjugate Chem.* (1998) 9:805-812.
Wang. "Solvent-dependent aggregation of a water-soluble poly (fluorene) controls energy transfer to chromophore-labeled DNA", Chern. Comm, R. Soc. Chern., 2508-2509, 2004.
Wang, et al. "Photoluminescence of Water-Soluble Conjugated Polymers: Origin of Enhanced Quenching by Charge Transfer", *Macromolecules.* (2000) 33:5153-5158.
Wang, "Fluorescein provides a resonance gate for FRET from conjugated polymers to DNA intercalated dyes", JACS, 126(7):5446-5451, 2004.
Wang, et al., "Biosnesors from conjugated polyelectrolyte complexes", PNAS, 2002, 99(1), 49-53.
Wang, et al., "Size-Specific Interactions Between Single- and Double-Stranded Oligonucleotides and Cationic Water-Soluble Oligofluorenes", Adv. Funct. Mater., Jun. 2003, 13(6), 463-467.
Wang, "Survey and Summary From DNA biosensors to gene chips", Nucleic Acids Research, 2000, 28(16), 3011-3016.
Wang, et al., "Optically Amplified RNA-Protein Detection Methods Using Light-Harvesting Conjugated Polymers", Adv. Mater., Sep. 2003, 15(17), 1425-1428.
Wang, et al. "DNA Electrochemical Biosensor for the Detection of Short DNA Sequences Related to the Human Immunodeficiency Virus", *Anal. Chem.* (1996) 68:15:2629-2634.
Wang, et al. "Synthesis of AB(BA), ABA and BAB Block Copolymers of tert-Butyl Methacrylate (A) and Ethylene Oxide (B)", *J. Polym. Sci., Part A: Polym. Chem.* (1992) 30:2251-2261.
Wang, et al. "Interaction of DNA with Cationic Micelles: Effects of Micelle Surface Charge Density, Micelle Shape, and Ionic Strength on Complexation and DNA Collapse" *Langmuir.* (2001) 17:1670-1673.
Waring, M. J. "Complex Formation between Ethidium Bromide and Nucleic Acids", *J. Mol. Bioi.* (1965) 13:269-282.
Weeks, et al. "Fragments of the HIV-1 Tat Protein Specifically Bind TAR RNA", *Science.* (1990) 249:1281-1285.
Whitcombe, et al. "Detection of PCR products using self-probing amplicons and fluorescence" *Nat. Biotechnol.*(1999) 17;804-807.
Wolcott, "Advances in Nucleic Acid-Based Detection Methods", Clinical Microbiology Reviews, Oct. 1992, 5(4), 370-386.
Wolfert, et al. "Polyelectrolyte Vectors for Gene Delivery: Influence of Cationic Polymer on Biophysical Properties of Complexes Formed with DNA", *Bioconjugate* Chern. (1999) 10:993-1004.
Wyman, et al. "Design, Synthesis, and Characterization of a Cationic Peptide that Binds to Nucleic Acids and Permeabilizes Bilayers" *Biochemistry.* (1997) 36:3008-3017.
Wintermeyer, et al., "Fluorescent Derivatives of Yeast tRNA(TM)", Eur. J. Biochem., 1979, 98, 465-475.
Xu, et al., "Immobilization and Hybridization of DNA on an Aluminum(III) Alkanebisphosphonate Thin Film with Electrogenerated Chemiluminescent Detection", *J. Am. Chern. Soc.* (1995) 117:2627-2631.
Yang, et al., "Fluorescent Porous Polymer Films as TNT Chemosensors: Etectronic and Structural Effects", *J. Am. Chern. Soc.* (1998) 120:11864-11873.

(56) References Cited

OTHER PUBLICATIONS

Zhou, et al., "Methodology for Enhancing the Sensitivity of Fluorescent Chemosensors: Energy Migration in Conjugated Polymers", J. Am. Chem. Soc., 1995, 117, 7017-7018.
Zhou et al., "Fluorescent Chemosensors Based on Energy Migration in Conjugated Polymers: The Molecular Wire Approach to Increased Sensitivity", J. Am. Chem. Soc., 1995, 117, 12593-12602.
International Search Report issued Apr. 14, 2004 in PCT/US2003/019678.
Supplementary EP Search Report issued Sep. 27, 2007 in EP 03761235.5.
Office action issued Oct. 20, 2006 in CN03819836.3.
Office action issued Sep. 25, 2008 in CN03819836.3.
Examination Report issued Jul. 17, 2008 in EP 03761235.5.
First Office Action issued Mar. 17, 2009 in JP 2004-516105.
Examination Report issued Aug. 31, 2006 in NZ 537707.
Written Opinion issued Oct. 7, 2005 and response thereto filed Mar. 6, 2006 in SG 200407571-9.
Examination report issued Jun. 26, 2006 in SG 200407571-9.
International Search Report and Written Opinion issued Mary 12, 2005 in PCT/US2004/04286.
International Preliminary Report on Patentability issued Aug. 19, 2005 in PCT/US2004/04286.
First Office Action issued Apr. 13, 2007 in CN 200480009631.4.
Supplementary EP Search Report issued Sep. 27, 2007 in EP 04737272.7.
International Search Report and Written Opinion issued Dec. 16, 2005 in PCT/US2004/030605.
International Preliminary Report on Patentability issued Mar. 21, 2006 in PCT/US2004/030605.
Examination report issued Sep. 10, 2008 and response thereto filed Mar. 20, 2009 in EP 04821601.4.
International Search Report issued Mar. 18, 2005 in PCT/US2003/026989.
First Office Action issued Apr. 28, 2005 in CN 03824651.1.
Decision on Rejection issued Jul. 6, 2007 in CN 03824651.1.
Request for Reexamination filed Oct. 18, 2007 in CN 03824651.1.
Supplementary European Search Report issued Sep. 20, 2007 in EP 03816297.
Official Action issued Jul. 17, 2008 in EP 03816297.
International Search Report and Written Opinion issued Dec. 12, 2006 in PCT/US2006/00928.
International Preliminary Report on Patentability issued Jul. 10, 2007 in PCT/US2006/00928.
International Search Report and Written Opinion issued Aug. 16, 2006 in PCT/US2006/00882.
International Preliminary Report on Patentability issued Jul. 10, 2007 in PCT/US2006/00882.
International Search Report and Written Opinion issued Sep. 11, 2006 in PCT/US2006/003498.
International Preliminary Report on Patentability issued Jul. 31, 2007 in PCT/US2006/003498.
Examination Report issued Jan. 17, 2008 and response thereto filed Jul. 25, 2008 in EP 04737272.7.
Clegg, et al., "Fluorescence Resonance Energy Transfer Analysis of the Structure of the Four-Way DNA Junction", Biochemistry, 1992;31(20):4846-56.
Life Technologies, Fluorescence SpectraViewer, displaying FITC emission and TAMRA excitation spectra. Datasheet, 2014, 2 Pages.

METHODS AND COMPOSITIONS FOR DETECTION AND ANALYSIS OF POLYNUCLEOTIDES USING LIGHT HARVESTING MULTICHROMOPHORES

CROSS REFERENCE TO RELATED APPLICATIONS

This application is a continuation of U.S. patent application Ser. No. 11/854,365, filed Sep. 12, 2007, now U.S. Pat. No. 7,629,448 issued Dec. 8, 2009, which claims the benefit of U.S. patent application Ser. No. 10/648,945 filed Aug. 26, 2003, now U.S. Pat. No. 7,270,956, issued Sep. 18, 2007, and of U.S. Provisional Application No. 60/406,266, filed Aug. 26, 2002. The aforementioned applications are hereby incorporated herein by reference in their entirety.

STATEMENT REGARDING FEDERALLY SPONSORED RESEARCH

This invention was made with Government support under grant number DMR-0097611 awarded by the National Science Foundation. The Government has certain rights in this invention.

TECHNICAL FIELD

This invention relates to methods, articles and compositions for the detection and analysis of polynucleotides in a sample.

BACKGROUND OF THE INVENTION

Methods permitting DNA sequence detection in real time and with high sensitivity are of great scientific and economic interest.[1,2,3] Their applications include medical diagnostics, identification of genetic mutations, gene delivery monitoring and specific genomic techniques.[4] Cationic organic dyes, such as ethidium bromide and thiazole orange, emit when intercalated into the grooves of double strand DNA (dsDNA), and serve as direct DNA hybridization probes, but lack sequence specificity.[5,6] Energy/electron transfer chromophore pairs for strand specific assays exist, but require chemical labeling of two nucleic acids, or dual modification of the same altered strand (for example, molecular beacons).[7,8] Difficulties in labeling two DNA sites result in low yields, high costs and singly labeled impurities, which lower detection sensitivity.[9]

There is a need in the art for methods of detecting and analyzing particular polynucleotides in a sample, and for compositions and articles of manufacture useful in such methods.

SUMMARY OF THE INVENTION

Methods, compositions and articles of manufacture for detecting and assaying a target polynucleotide in a sample are provided.

A sample suspected of containing the target polynucleotide is contacted with a polycationic multichromophore and a sensor polynucleotide complementary to the target polynucleotide. The sensor polynucleotide comprises an anionic backbone, such as a typical sugar phosphate backbone, and is conjugated to a signaling chromophore. In the presence of target polynucleotide in the sample, the signaling chromophore can acquire energy more efficiently from the excited polycationic multichromophore and emit increased amounts of light or signal which can be detected. The target polynucleotide can be analyzed as it occurs in the sample, or can be amplified prior to or in conjunction with analysis.

Although the anionic sensor can associate with the cationic multichromophore in the absence of target, a surprising increase in signal has been found to occur upon binding of the target polynucleotide to form a double-stranded complex relative to the signal produced from a mixture of non-complementary sequences. This increase in signal can be exploited for use in detection methods for assaying for a target polynucleotide in a sample.

Solutions are provided comprising reagents useful for performing the methods of the invention, as are kits containing such reagents. Also provided are sensing or detection complexes formed from the multichromophore and sensor polynucleotide, and signaling complexes further comprising the target polynucleotide. The methods can be used in multiplex settings where a plurality of different sensor polynucleotides are used to assay for a plurality of different target polynucleotides. The methods can optionally be performed on a surface, for example using a surface-associated polycationic multichromophore; the surface can be a sensor. The methods can also be provided in homogeneous formats. The methods and articles described herein can be used as alternatives to other techniques for detecting polynucleotides.

DETAILED DESCRIPTION OF THE INVENTION

Figure 1:
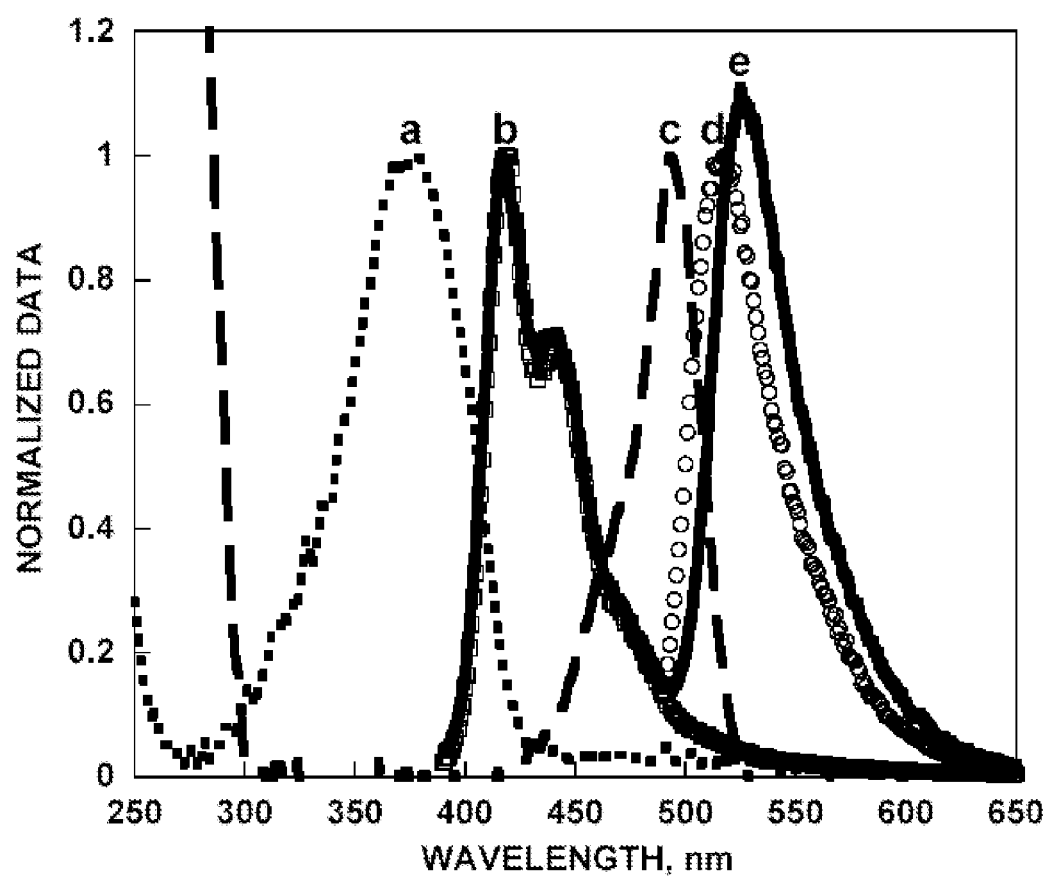
FIG. 1 depicts the absorption (a (dotted line) and c (dashed line)) and emission (b (squares) and d (circles)) spectra of polymer 1 and a fluorescein-conjugated sensor polynucleotide. Excitation was done at 380 and 480 nm for polymer 1 and sensor polynucleotide, respectively. The energy transfer complex of polymer 1 and sensor polynucleotide excited at 380 nm is also shown in black (e, solid line).
Figure 2:
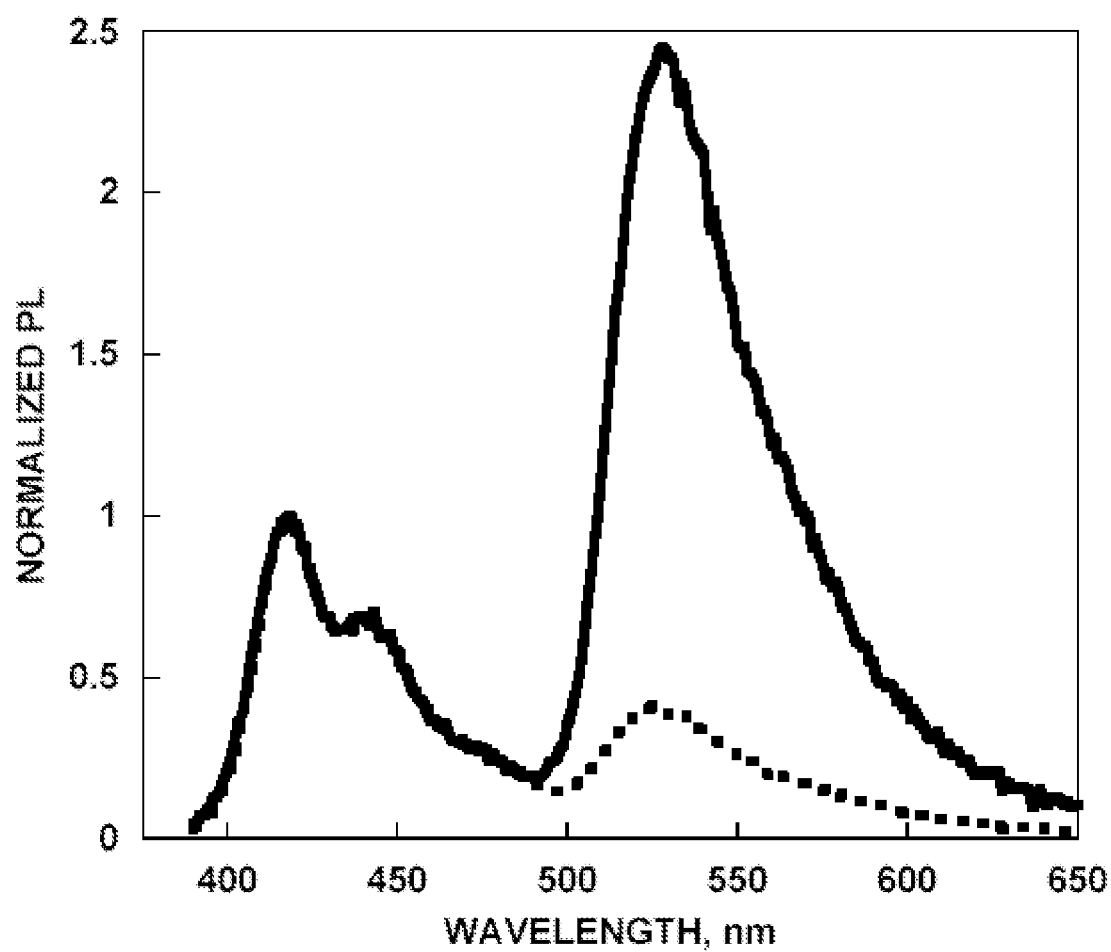
FIG. 2 presents the emission spectra of the sensor system containing hybridized (solid line) and non-hybridized (dotted line) sensor polynucleotides in 10 mmol Sodium Citrate and 100 mmol sodium chloride buffer at pH=8. Spectra are normalized relative to the emission of polymer 1.
Figure 3:
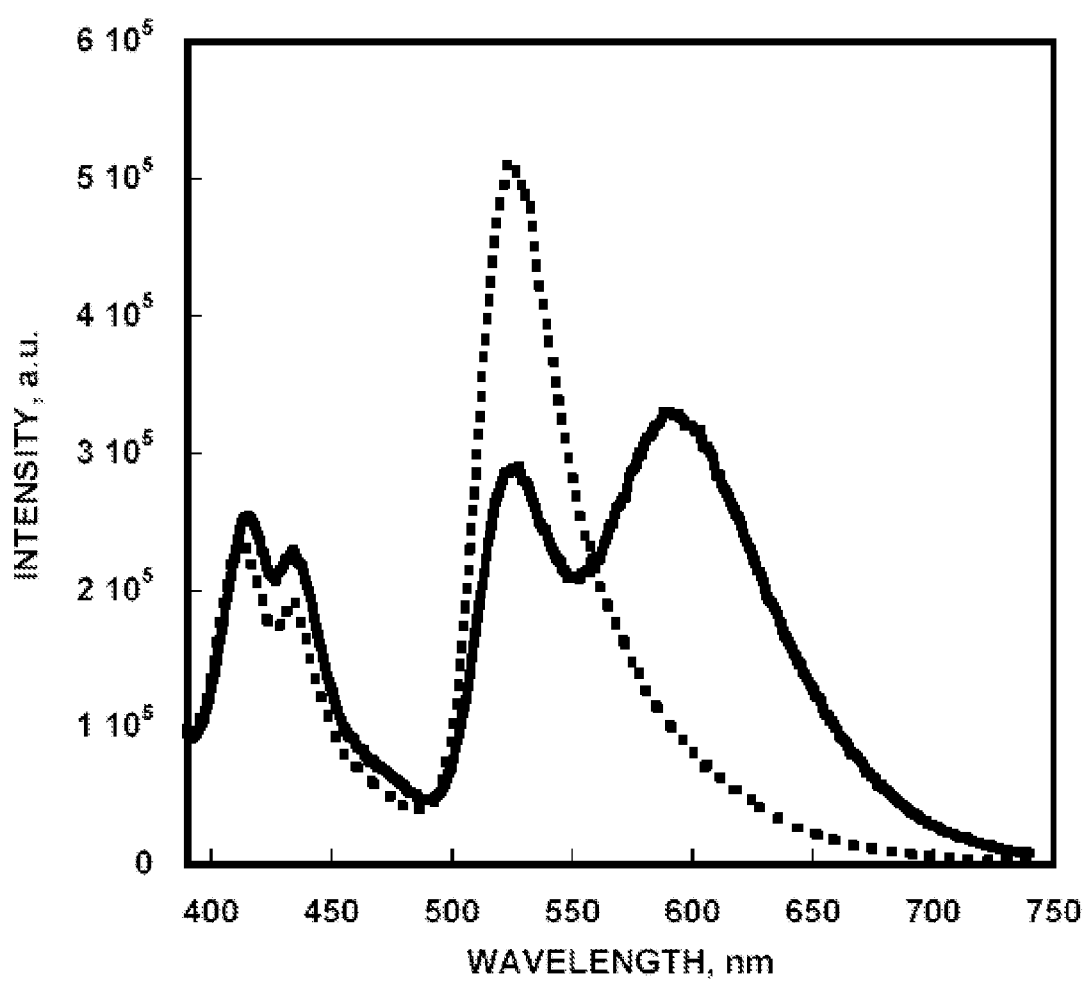
FIG. 3 depicts the emission spectra of the sensor system containing hybridized (solid line) and non-hybridized (dotted line) sensor polynucleotides resulting from excitation of the multichromophore (polymer 1) and energy transfer to the sensor polynucleotide followed by subsequent energy transfer to a polynucleotide specific dye (Ethidium Bromide). Measurements are in potassium phosphate-sodium hydroxide buffer solution (50 mM, pH=7.40). See Example 4.

Present technologies for DNA and RNA sensors (including "gene-chips" and "DNA-chips") depend on the covalent attachment of fluorescent tags (lumophores) to single strands of DNA, relying on labeling of the sample or a sample component, with unavoidable problems resulting from variations in the efficiency of the labeling reaction from sample to sample, requiring complex cross-calibrations. Other systems rely on multiply labeled probes (e.g., molecular beacons, Taqman®, Scorpion® probes, Eclipse® probes), requiring the multiple attachment of lumophores and quenchers to precisely engineered sequences.

The method of the invention comprises contacting a sample with an aqueous solution comprising at least two components; (a) a light harvesting, polycationic, luminescent multichromophore system such as, for example, a conjugated polymer, semiconductor quantum dot or dendritic structure that is water soluble, and (b) a sensor polynucleotide conjugated to a luminescent signaling chromophore (referred to as "Oligo-C*"). The emission of light with wavelength characteristic of the signaling chromophore indicates the presence in solution of a target polynucleotide with a base sequence complementary to that of the sensor polynucleotide. By using multiple sensor polynucleotides, each with a different base sequence and a different signaling chromophore ($Oligo_1$-$C_1^*$, $Oligo_2$-$C_2^*$, etc), multiple polynucleotides each with specific base sequences can be independently detected. A third component such as a polynucleotide-specific dye may be introduced to improve selectivity by further transferring energy from the sensor polynucleotide to the polynucleotide-specific dye.

The light harvesting chromophore and the signaling chromophore (C*) are chosen so that the absorption bands of the two species have minimal overlap and so that the luminescent emission spectra of the two species are at different wavelengths. When prepared in aqueous solution, the light harvesting and luminescent multi-chromophore systems are positively charged (for example positively charged conjugated polyelectrolytes). The proximity between a negatively charged sensor polynucleotide and a positively charged light harvesting and luminescent multi-chromophore system is ensured by electrostatic attraction. When exposed to incident radiation with wavelength in the absorption band of the light harvesting chromophore, there is emission from the signaling chromophore, for example via the Förster energy transfer mechanism. Upon addition of a target polynucleotide such as a single stranded DNA (ssDNA) with a base sequence that is complementary to the sequence of the sensor polynucleotide, the ssDNA hybridizes with the sensor polynucleotide resulting in an increase in negative charge density along the DNA strand.[10,11] Under these circumstances, and considering strictly electrostatic forces, the interaction between the sensor polynucleotide and the positively charged light harvesting multi-chromophore system will be favorable, leading to efficient energy transfer and intense emission from the signaling chromophore. When ssDNA with a base sequence that is not complementary to that of the sensor polynucleotide is added, base pair hybridization does not take place. Electrostatic complexation between a light harvesting multi-chromophore system and a sensor polynucleotide is screened by competition with the non-complementary ssDNA. Thus, the average distance between the light harvesting multi-chromophore system and the Oligo-C* is larger in the presence of a non-complementary sequence, resulting in less effective energy transfer to the signaling chromophore. The emission of the signaling Oligo-C* is stronger when in the presence of its complementary target than when a non-complementary strand is present. The overall scheme provides a sensor for the presence of a target polynucleotide with a specific base sequence in the test solution. By using multiple sensor polynucleotides, each with a different base sequence and a different signaling chromophore, multiple targets can be separately detected.

In addition to the described method, the invention provides a predominantly aqueous solution comprising at least two components; (a) a cationic multichromophore, and (b) a "sensor polynucleotide" (Oligo-C*) comprising an anionic polynucleotide conjugated to a signaling chromophore.

As demonstrated in the Examples, the optical amplification provided by a water soluble multichromophore such as a conjugated polymer can be used to detect polynucleotide hybridization to a sensor polynucleotide. The amplification can be enhanced by using higher molecular weight water soluble conjugated polymers or other structures as the polycationic multichromophore as described herein. The invention can be provided in a homogeneous format that utilizes the ease of fluorescence detection methods. The invention can be used to detect amplified target polynucleotides or, because of the large signal amplification, as a stand alone assay, without need for polynucleotide amplification.

Unlike gene-chip technology, the present invention does not necessarily require labeling of each sample to be analyzed by covalent coupling of lumophores or chromophores to the polynucleotides contained in or derived from the sample prior to analysis. Those coupling methods have inherent difficulties in reproducibility of coupling efficiency and result in the need for cross-calibration from sample to sample.

The inventions described herein are useful for any assay in which a sample can be interrogated regarding a target polynucleotide. Typical assays involve determining the presence of the target polynucleotide in the sample or its relative amount, or the assays may be quantitative or semi-quantitative.

The methods of the invention can all be performed in multiplex formats. A plurality of different sensor polynucleotides can be used to detect corresponding different target polynucleotides in a sample through the use of different signaling chromophores conjugated to the respective sensor polynucleotides. Multiplex methods are provided employing 2, 3, 4, 5, 10, 15, 20, 25, 50, 100, 200, 400 or more different sensor polynucleotides which can be used simultaneously to assay for corresponding different target polynucleotides.

The methods can be performed on a substrate, as well as in solution, although the solution format is expected to be more rapid due to diffusion issues. Thus the assay can be performed, for example, in an array format on a substrate, which can be a sensor. This can be achieved by anchoring or otherwise incorporating an assay component onto the substrate, for example the sensor polynucleotide, the polycationic multichromophore, or both. These substrates may be surfaces of glass, silicon, paper, plastic, or the surfaces of optoelectronic semiconductors (such as, but not confined to, indium-doped gallium nitride or polymeric polyanilines, etc.) employed as optoelectronic transducers. The location of a given sensor polynucleotide may be known or determinable in an array format, and the array format may be microaddressable or nanoaddressable. In one variation, one or more samples, which may contain an amplification product, can be attached to the substrate, and the substrate can be contacted with one or more labeled sensor polynucleotides and the polycationic multichromophore.

Before the present invention is described in further detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a target polynucleotide" includes a plurality of target polynucleotides, reference to "a signaling chromophore" includes a plurality of such chromophores, reference to "a sensor polynucleotide" includes a plurality of sensor polynucleotides, and the like. Additionally, use of specific plural references, such as "two," "three," etc., read on larger numbers of the same subject less the context clearly dictates otherwise.

Terms such as "connected," "attached," and "linked" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

Definitions

In describing the present invention, the following terms will be employed, and are intended to be defined as indicated below.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer only to the primary structure of the molecule. Thus, the terms includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide.

Whether modified or unmodified, the sensor polynucleotide is anionic and can interact with the cationic multichromophore in the absence of target polynucleotide. The target polynucleotide can in principle be charged or uncharged, although typically it is expected to be anionic, for example RNA or DNA.

More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing a phosphate or other polyanionic backbone, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA, and also include known types of modifications, for example, labels, alkylation, "caps," substitution of one or more of the nucleotides with an analog, internucleotide modifications such as, for example, those with negatively charged linkages (e.g., phosphorothioates, phosphorodithioates, etc.), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide; preferably the polynucleotide does not comprise abasic sites. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described in U.S. Pat. No. 5,780,610 to Collins et al. Other nonnatural base pairs may be synthesized by the method described in Piccirilli et al. (1990) Nature 343:33-37 for the synthesis of 2,6-diaminopyrimidine and its complement (1-methylpyrazolo-[4,3]pyrimidine-5,7-(4H,6H)-dione). Other such modified nucleotidic units which form unique base pairs are known, such as those described in Leach et al. (1992) J. Am. Chem. Soc. 114:3675-3683 and Switzer et al., supra.

"Preferential binding" or "preferential hybridization" refers to the increased propensity of one polynucleotide or PNA to bind to its complement in a sample as compared to a noncomplementary polymer in the sample.

Hybridization conditions will typically include salt concentrations of less than about 1M, more usually less than about 500 mM and preferably less than about 200 mM. In the case of hybridization between a peptide nucleic acid and a polynucleotide, the hybridization can be done in solutions containing little or no salt. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Suitable hybridization conditions for a given assay format can be determined by one of skill in the art; nonlimiting parameters which may be adjusted include concentrations of assay components, salts used and their concentration, ionic strength, temperature, buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method in which multiple analytes can be assayed simultaneously.

"Optional" or "optionally" means that the subsequently described event or circumstance may or may not occur, and that the description includes instances where the event or circumstance occurs and instances in which it does not.

The Sample

The portion of the sample comprising or suspected of comprising the target polynucleotide can be any source of biological material which comprises polynucleotides that can be obtained from a living organism directly or indirectly, including cells, tissue or fluid, and the deposits left by that organism, including viruses, mycoplasma, and fossils. The sample may comprise a target polynucleotide prepared through synthetic means, in whole or in part. Typically, the sample is obtained as or dispersed in a predominantly aqueous medium. Non-limiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant library comprising polynucleotide sequences. The sample may be presented on a substrate as described herein. The substrate may be a slide comprising the sample, such as is used in fluorescence in situ hybridization (FISH).

The sample can be a positive control sample which is known to contain the target polynucleotide or a surrogate thereof. A negative control sample can also be used which, although not expected to contain the target polynucleotide, is suspected of containing it (via contamination of one or more of the reagents) or another component capable of producing a false positive, and is tested in order to confirm the lack of contamination by the target polynucleotide of the reagents used in a given assay, as well as to determine whether a given set of assay conditions produces false positives (a positive signal even in the absence of target polynucleotide in the sample).

The sample can be diluted, dissolved, suspended, extracted or otherwise treated to solubilize and/or purify any target polynucleotide present or to render it accessible to reagents which are used in an amplification scheme or to detection reagents. Where the sample contains cells, the cells can be lysed or permeabilized to release the polynucleotides within the cells. One step permeabilization buffers can be used to lyse cells which allow further steps to be performed directly after lysis, for example a polymerase chain reaction.

The Target Polynucleotide and Amplification Products Produced Therefrom

The target polynucleotide can be single-stranded, double-stranded, or higher order, and can be linear or circular. Exemplary single-stranded target polynucleotides include mRNA, rRNA, tRNA, hnRNA, ssRNA or ssDNA viral genomes, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phage, and viroids. The target polynucleotide can be prepared synthetically or purified from a biological source. The target polynucleotide may be purified to remove or diminish one or more undesired components of the sample or to concentrate the target polynucleotide. Conversely, where the target polynucleotide is too concentrated for the particular assay, the target polynucleotide may be diluted.

Following sample collection and optional nucleic acid extraction, the nucleic acid portion of the sample comprising the target polynucleotide can be subjected to one or more preparative reactions. These preparative reactions can include in vitro transcription (IVT), labeling, fragmentation, amplification and other reactions. mRNA can first be treated with reverse transcriptase and a primer to create cDNA prior to detection and/or amplification; this can be done in vitro with purified mRNA or in situ, e.g. in cells or tissues affixed to a slide. Nucleic acid amplification increases the copy number of sequences of interest such as the target polynucleotide. A variety of amplification methods are suitable for use; nonlimiting examples of suitable amplification reactions include the polymerase chain reaction method (PCR), the ligase chain reaction (LCR), self sustained sequence replication (3SR), nucleic acid sequence-based amplification (NASBA), the use of Q Beta replicase, reverse transcription, nick translation, and the like.

Where the target polynucleotide is single-stranded, the first cycle of amplification forms a primer extension product complementary to the target polynucleotide. If the target polynucleotide is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide is typically amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity which can copy the target polynucleotide can be used, including DNA polymerases, RNA polymerases, reverse transcriptases, enzymes having more than one type of polymerase activity, and the enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse IT MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfx, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

Amplified target polynucleotides may be subjected to post amplification treatments. For example, in some cases, it may be desirable to fragment the target polynucleotide prior to hybridization in order to provide segments which are more readily accessible. Fragmentation of the nucleic acids can be carried out by any method producing fragments of a size useful in the assay being performed; suitable physical, chemical and enzymatic methods are known in the art.

An amplification reaction can be performed under conditions which allow the sensor polynucleotide to hybridize to the amplification product during at least part of an amplification cycle. When the assay is performed in this manner, real-time detection of this hybridization event can take place by monitoring for a change in light emission from the signaling chromophore that occurs upon such hybridization during the amplification scheme.

The Polycationic Multichromophore

Light harvesting multichromophore systems have been demonstrated to be efficient light absorbers by virtue of the multiple chromophores they comprise. Examples include, but are not limited to, conjugated polymers, aggregates of conjugated molecules, luminescent dyes attached to saturated polymers, semiconductor quantum dots and dendritic structures. For example, each repeat unit on a conjugated polymer can be considered as a contributing chromophore, quantum dots are made up of many atoms, a saturated polymer can be functionalized with many luminescent dye molecules on side chains, and dendrimers can be synthesized containing many covalently bonded individual chromophores. Attachment of chromophore assemblies onto solid supports, such as polymer beads or surfaces, can also be used for light harvesting.

Light harvesting multichromophore systems can efficiently transfer energy to nearby luminescent species (e.g., "signaling chromophores"). Mechanisms for energy transfer include, for example, resonant energy transfer (Förster (or fluorescence) resonance energy transfer, FRET), quantum charge exchange (Dexter energy transfer) and the like. Typically, however, these energy transfer mechanisms are relatively short range; that is, close proximity of the light harvesting multichromophore system to the signaling chromophore is required for efficient energy transfer. Under conditions for efficient energy transfer, amplification of the emission from the signaling chromophore occurs when the number of individual chromophores in the light harvesting multichromophore system is large; that is, the emission from the signaling chromophore is more intense when the incident light (the "pump light") is at a wavelength which is absorbed by the light harvesting multichromophore system than when the signaling chromophore is directly excited by the pump light.

Conjugated polymers (CPs) are characterized by a delocalized electronic structure and can be used as highly responsive optical reporters for chemical and biological targets.[12,13] Because the effective conjugation length is substantially shorter than the length of the polymer chain, the backbone contains a large number of conjugated segments in close proximity. Thus, conjugated polymers are efficient for light harvesting and enable optical amplification via Förster energy transfer.[14]

Spontaneous interpolymer complexation between cationic polyelectrolytes and DNA has been described and is largely the result of cooperative electrostatic forces.[15,16,17] Hydrophobic interactions between aromatic polymer units and DNA bases were also recently recognized.[18,19] The free energy of polyelectrolyte/DNA interactions is controlled by the structure of the participating species used in conjunction with solution variables such as pH, ionic strength, and temperature.[20] The strength and specificity of these interactions has recently been coordinated to recognize the tertiary structure of plasmid DNA.[21]

The multichromophores used in the present invention are polycationic and can interact with a sensor polynucleotide electrostatically. Any polycationic multichromophore that can absorb light and transfer energy to a signaling chromophore on a sensor polynucleotide can be used in the methods described. Exemplary multichromophores which can be used include conjugated polymers, saturated polymers or dendrimers incorporating multiple chromophores in any viable manner, and semiconductor nanocrystals (SCNCs). The conjugated polymers, saturated polymers and dendrimers can be prepared to incorporate multiple cationic species or can be derivatized to render them polycationic after synthesis; semiconductor nanocrystals can be rendered polycationic by addition of cationic species to their surface.

In a preferred embodiment, a conjugated polymer is used as the polycationic multichromophore. A specific example is shown in structure 1 where the cationic water soluble conjugated polymer is poly((9,9-bis(6'-N,N,N-trimethylammonium)-hexyl)-fluorene phenylene) with iodide counteranions (denoted in the following as polymer 1).[22] The particular size of this polymer is not critical, so long as it is able to absorb light and transfer energy to signaling chromophores brought into proximity. Typical values of "n" fall within the range of two to about 100,000. This specific molecular structure is not critical; any water soluble cationic conjugated polymer with adequate luminescence quantum efficiency can be used.

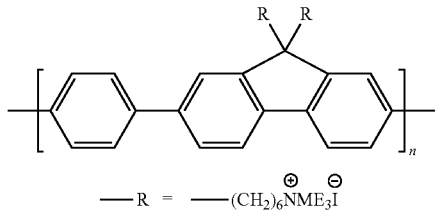

Water soluble conjugated oligomers can also be used as the polycationic multichromophore. An example of such a water soluble, cationic, luminescent conjugated oligomer with iodide counterions is shown below (denoted herein as oligomer 2):

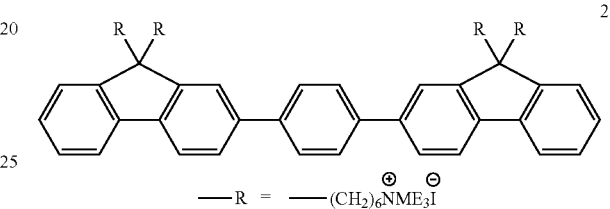

Although the smaller oligomer 2 does not display the large signal amplification characteristic of a high molecular weight polymer, such smaller molecules are useful to deconvolute structure property relationships, which are difficult to determine with the inherent polydispersity and batch-to-batch variations found in polymers. Further, in aqueous media oligomers such as 2 are more soluble than their polymeric counterparts, and hydrophobic interactions are expected to be less important for 2 than for polymer structures. Assemblies of oligomers may thus be desirably used for specific applications. Addition of organic solvents, for example a water miscible organic solvent such as ethanol, can result in a decrease in background C* emission. The presence of the organic solvent can decrease hydrophobic interactions and reduce background C* emission.

The Sensor Polynucleotide

A sensor polynucleotide is provided that is anionic and is complementary to the target polynucleotide to be assayed, and has a predetermined sequence. The sensor polynucleotide can be branched, multimeric or circular, but is typically linear, and can contain nonnatural bases. The sensor polynucleotide can be prepared with any desired sequence of bases. Chemical methods for attaching the signaling chromophore to the sensor polynucleotide are known in the art.[23] Specific sensor polynucleotide structures, including structures conjugated to chromophores, can be custom-made using commercial sources or chemically synthesized.

The Signaling Chromophore

Chromophores useful in the inventions described herein include any substance which can absorb energy from a polycationic multichromophore in an appropriate solution and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Exemplary fluorescent dyes include fluorescein, 6-FAM, rhodamine, Texas Red, tetramethylrhodamine, carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof, and combinations thereof. Exemplary lanthanide chelates include europium chelates, terbium chelates and samarium chelates.

A wide variety of fluorescent semiconductor nanocrystals ("SCNCs") are known in the art; methods of producing and utilizing semiconductor nanocrystals are described in: PCT Publ. No. WO 99/26299 published May 27, 1999, inventors Bawendi et al.; U.S. Pat. No. 5,990,479 issued Nov. 23, 1999 to Weiss et al.; and Bruchez et al., Science 281:2013, 1998. Semiconductor nanocrystals can be obtained with very narrow emission bands with well-defined peak emission wavelengths, allowing for a large number of different SCNCs to be used as signaling chromophores in the same assay, optionally in combination with other non-SCNC types of signaling chromophores.

Exemplary polynucleotide-specific dyes include acridine orange, acridine homodimer, actinomycin D, 7-aminoactinomycin D (7-AAD), 9-amino-6-chloro-2-methoxyacridine (ACMA), BOBO™-1 iodide (462/481), BOBO™-3 iodide (570/602), BO-PRO™-1 iodide (462/481), BO-PRO™-3 iodide (575/599), 4',6-diamidino-2-phenylindole, dihydrochloride (DAPI), 4',6-diamidino-2-phenylindole, dihydrochloride (DAPI), 4',6-diamidino-2-phenylindole, dilactate (DAPI, dilactate), dihydroethidium (hydroethidine), dihydroethidium (hydroethidine), dihydroethidium (hydroethidine), ethidium bromide, ethidium diazide chloride, ethidium homodimer-1 (EthD-1), ethidium homodimer-2 (EthD-2), ethidium monoazide bromide (EMA), hexidium iodide, Hoechst 33258, Hoechst 33342, Hoechst 34580, Hoechst S769121, hydroxystilbamidine, methanesulfonate, JOJO™-1 iodide (529/545), JO-PRO™-1 iodide (530/546), LOLO™-1 iodide (565/579), LO-PRO™-1 iodide (567/580), NeuroTrace™ 435/455, NeuroTrace™ 500/525, NeuroTrace™ 515/535, NeuroTrace™ 530/615, NeuroTrace™ 640/660, OliGreen, PicoGreen® ssDNA, PicoGreen® dsDNA, POPO™-4 iodide (434/456), POPO™-3 iodide (534/570), PO-PRO™-1 iodide (435/455), POPRO™-3 iodide (539/567), propidium iodide, RiboGreen®, SlowFade®, SlowFade® Light, SYBR® Green I, SYBR® Green II, SYBR® Gold, SYBR® 101, SYBR® 102, SYBR® 103, SYBR® DX, TO-PRO®-1, TO-PRO®-3, TO-PRO®-5, TOTO®-1, TOTO®-3, YO-PRO®-1 (oxazole yellow), YO-PRO®-3, YOYO®-1, YOYO®-3, TO, SYTOX® Blue, SYTOX® Green, SYTOX® Orange, SYTO® 9, SYTO® BC, SYTO® 40, SYTO® 41, SYTO® 42, SYTO® 43, SYTO® 44, SYTO® 45, SYTO® Blue, SYTO® 11, SYTO® 12, SYTO® 13, SYTO® 14, SYTO® 15, SYTO® 16, SYTO® 20, SYTO® 21, SYTO® 22, SYTO® 23, SYTO® 24, SYTO® 25, SYTO® Green, SYTO® 80, SYTO® 81, SYTO® 82, SYTO® 83, SYTO® 84, SYTO® 85, SYTO® Orange, SYTO® 17, SYTO® 59, SYTO® 60, SYTO® 61, SYTO® 62, SYTO® 63, SYTO® 64, SYTO® Red, netropsin, distamycin, acridine orange, 3,4-benzopyrene, thiazole orange, TOMEHE, daunomycin, acridine, pentyl-TOTAB, and butyl-TOTIN. Asymmetric cyanine dyes may be used as the polynucleotide-specific dye. Other dyes of interest include those described by Geierstanger, B. H. and Wemmer, D. E., Annu. Rev. Vioshys. Biomol. Struct. 1995, 24, 463-493, by Larson, C. J. and Verdine, G. L., Bioorganic Chemistry Nucleic Acids, Hecht, S. M., Ed., Oxford University Press: New York, 1996; pp 324-346, and by Glumoff, T. and Goldman, A. Nucleic Acids in Chemistry and Biology, $2^{nd}$ ed., Blackburn, G. M. and Gait, M. J., Eds., Oxford University Press: Oxford, 1996, pp 375-441. The polynucleotide-specific dye may be an intercalating dye, and may be specific for double-stranded polynucleotides. Other dyes and fluorophores are described at www.probes.com (Molecular Probes, Inc.).

The term "green fluorescent protein" refers to both native *Aequorea* green fluorescent protein and mutated versions that have been identified as exhibiting altered fluorescence characteristics, including altered excitation and emission maxima, as well as excitation and emission spectra of different shapes (Delagrave, S. et al. (1995) Bio/Technology 13:151-154; Heim, R. et al. (1994) Proc. Natl. Acad. Sci. USA 91:12501-12504; Heim, R. et al. (1995) Nature 373:663-664). Delgrave et al. isolated mutants of cloned *Aequorea victoria* GFP that had red-shifted excitation spectra. Bio/Technology 13:151-154 (1995). Heim, R. et al. reported a mutant (Tyr66 to His) having a blue fluorescence (Proc. Natl. Acad. Sci. (1994) USA 91:12501-12504).

In one variation, a second signaling chromophore, which may be directly or indirectly attached to another of the assay components and/or to a substrate, is used to receive energy from the initial signaling chromophore. In particular applications, this can provide for significant additional selectivity. For example, a polynucleotide-specific dye can be used as either the initial or second signaling chromophore, and may be specific for double-stranded sequences. Energy can then be transferred from the excited cationic multichromophore to the initial signaling chromophore, which subsequently transfers energy to the second signaling chromophore, in an overall format that is selective for the target. This cascade of signaling chromophores can, in principle, be extended to use any number of signaling chromophores with compatible absorption and emission profiles. In one embodiment of this variation, an intercalating dye that is specific for double-stranded polynucleotides is used as the second signaling chromophore, and an initial signaling chromophore that is capable of transferring energy to the second signaling chromophore is conjugated to the sensor polynucleotide. The intercalating dye provides the added selective requirement that the sensor and target polynucleotides hybridize before it is recruited to the detection complex. In the presence of target, the duplex is formed, the dye is recruited, and excitation of the multichromophore leads to signaling from the second signaling chromophore.

The Substrate

The methods described herein can be performed on a substrate in any of a variety of formats. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, SiO$_2$, SiN$_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly (ethylene-co-vinyl acetate), polysiloxanes, polymeric silica, latexes, dextran polymers, epoxies, polycarbonates, agarose, poly(acrylamide) or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and includes semiconductor nanocrystals.

The substrate can take the form of a photodiode, an optoelectronic sensor such as an optoelectronic semiconductor chip or optoelectronic thin-film semiconductor, or a biochip. The location(s) of the individual sensor polynucleotide(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which a sensor polynucleotide or other assay component is located. The surface of the substrate can be etched using well known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface are chosen to provide appropriate optical characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

Sensor polynucleotides can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261.

Still further techniques include bead based techniques such as those described in PCT Appl. No. PCT/US93/04145 and pin based methods such as those described in U.S. Pat. No. 5,288,514.

Additional flow channel or spotting methods applicable to attachment of sensor polynucleotides to the substrate are described in U.S. patent application Ser. No. 07/980,523, filed Nov. 20, 1992, and U.S. Pat. No. 5,384,261. Reagents are delivered to the substrate by either (1) flowing within a channel defined on predefined regions or (2) "spotting" on predefined regions. A protective coating such as a hydrophilic or hydrophobic coating (depending upon the nature of the solvent) can be used over portions of the substrate to be protected, sometimes in combination with materials that facilitate wetting by the reactant solution in other regions. In this manner, the flowing solutions are further prevented from passing outside of their designated flow paths.

Typical dispensers include a micropipette optionally robotically controlled, an ink-jet printer, a series of tubes, a manifold, an array of pipettes, or the like so that various reagents can be delivered to the reaction regions sequentially or simultaneously.

Excitation and Detection of the Chromophores

Any instrument that provides a wavelength that can excite the polycationic multichromophore and is shorter than the emission wavelength(s) to be detected can be used for excitation. The excitation source preferably does not significantly excite the signaling chromophore directly. The source may be: a broadband UV light source such as a deuterium lamp with an appropriate filter, the output of a white light source such as a xenon lamp or a deuterium lamp after passing through a monochromator to extract out the desired wavelengths, a continuous wave (cw) gas laser, a solid state diode laser, or any of the pulsed lasers. The emitted light from the signaling chromophore can be detected through any suitable device or technique; many suitable approaches are known in the art. For example, a fluorometer or spectrophotometer may be used to detect whether the test sample emits light of a wavelength characteristic of the signaling chromophore upon excitation of the multichromophore.

Kits

Kits comprising reagents useful for performing the methods of the invention are also provided. In one embodiment, a kit comprises a single-stranded sensor polynucleotide that is complementary to a target polynucleotide of interest and a polycationic multichromophore. The sensor polynucleotide is conjugated to a signaling chromophore. In the presence of the target polynucleotide in the sample, the sensor polynucleotide hybridizes to the target, resulting in increased emission of energy from the signaling chromophore, which can be detected.

The components of the kit are retained by a housing. Instructions for using the kit to perform a method of the invention can be provided with the housing, and can be provided in any fixed medium. The instructions may be located inside the housing or outside the housing, and may be printed on the interior or exterior of any surface forming the housing which renders the instructions legible. The kit may be in multiplex form, containing pluralities of one or more different sensor polynucleotides which can hybridize to corresponding different target polynucleotides.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1

Identification of a FRET Scheme

Figure 4:
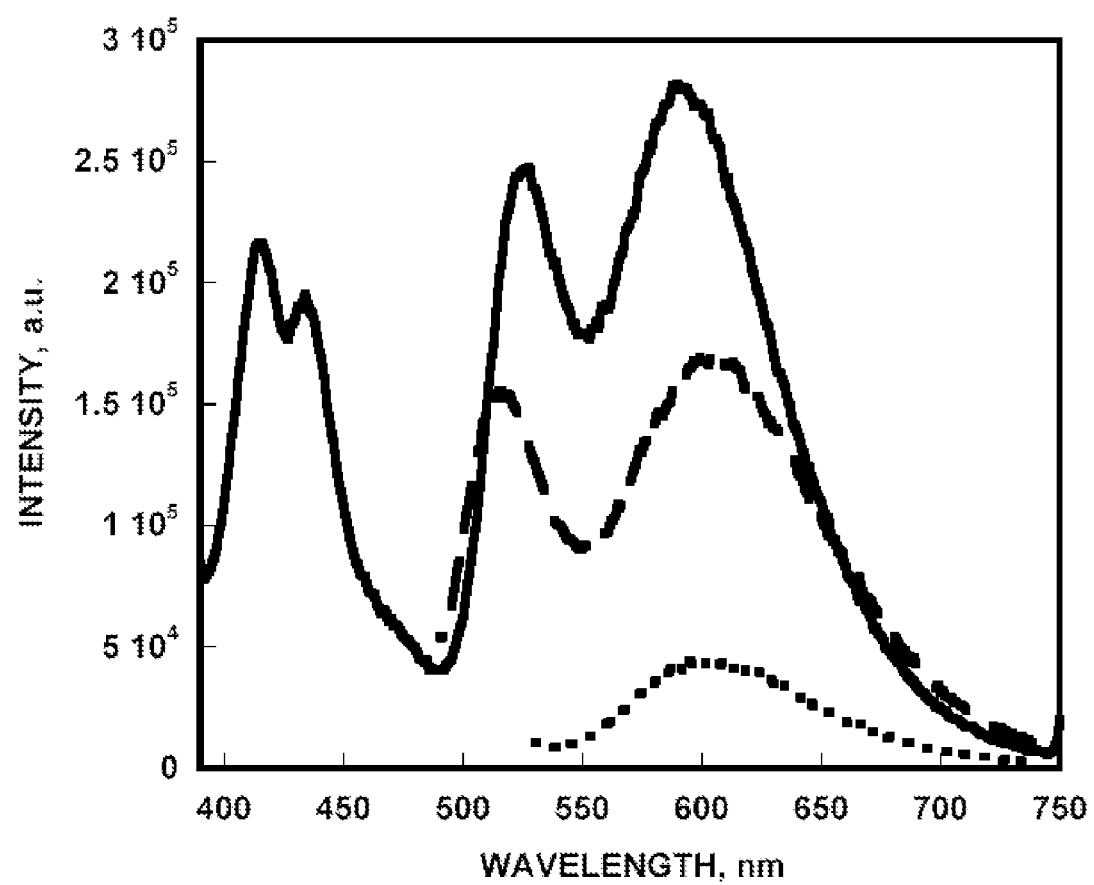
FIG. 4 depicts the amplified emission spectra of a polynucleotide-specific dye (Ethidium Bromide, EB) in the sensor system containing a hybridized (solid line) sensor polynucleotide. The amplified emission signal is a result of excitation of the multichromophore (polymer 1) and energy transfer to a sensor polynucleotide followed by subsequent energy transfer to EB. Direct EB emission in double stranded DNA (dotted line) and the emission resulting from sensor polynucleotide excitation followed by energy transfer to EB (dashed line) is shown to demonstrate the increased signal provided by the polycationic multichromophore. Measurements are in potassium phosphate-sodium hydroxide buffer solution (50 mM, pH=7.40). See Example 5.

Hybridization tests using energy transfer from the light harvesting multi-chromophore system to the signaling chromophore was demonstrated using the cationic water soluble conjugated polymer poly(9,9-bis(6'-N,N,N-trimethylammonium)-hexyl)-fluorene phenylene), polymer 1 with iodide counteranions. The sensor polynucleotide sequence was 5'-GTAAATGGTGTTAGGGTTGC-3' (SEQ ID NO: 1), corresponding to the anthrax (*Bacillus anthracis*) spore encapsulation plasmid, pX02, with fluorescein at the 5' position, forming an example of oligo-C*.[24] The absorption and emission spectra of the polymer and the signaling chromophore are shown in FIG. 1. The data show an optical window for the excitation of polymer 1, between the absorption of DNA and fluorescein. Direct excitation of polymer 1 results in energy transfer (ET) to fluorescein, as shown in FIG. 1. The absorbance overlap of fluorescein with the emission of polymer 1 was selected to ensure FRET.[25] The extent of ET can be evaluated by the ratio of integrated acceptor to donor emission.

Example 2

Demonstration of FRET in the Presence of Target Polynucleotide

Hybridization of the Oligo-C* probe leads to changes in the ET ratio. The sensor polynucleotide ([Oligo-C*]=$2.1\times10^{-8}$M) was annealed at 2° C. below its $T_m$ (58.4° C.) in the presence of an equal molar amount of a 40 base pair strand containing a complementary 20 base pair sequence, 5'-CATCTGTAAATCCAAGAGTAGCAACCCTAACACCATTTAC-3' (SEQ ID NO: 2), and in an identical fashion with a non-complementary 40 base strand with the sequence 5'-AAAATATTGTGTATCAAAATGTAAATGGTGTTAGGGTTGC-3' (SEQ ID NO: 3). Direct comparison of the resulting fluorescence reveals an ET ratio greater than 6 fold higher for the hybridized DNA. See FIG. 2. It is also highly significant that these optical differences are observed in the presence of a 10 mmol Sodium Citrate and 100 mmol Sodium Chloride buffer. Buffer ions screen like charges on complementary DNA strands which facilitates hybridization but weakens electrostatic interactions between CPs and fluorescence quenchers of opposite charge.[26] Using a Xenon lamp fluorometer, equipped with a standard PMT, the hybridized DNA provided over 3 fold greater ET ratios, at [sensor polynucleotide]=$2.8\times10^{-9}$M, than did the non-hybridized DNA.

Example 3

Optimization of Energy Transfer

Energy transfer was optimized by varying the ratio of polymer 1 to Oligo-C*. At a concentration of [Oligo-C*]=$2.1\times10^{-8}$M, initial additions of polymer cause an immediate rise in the ET ratio, which drops off as the amount of polymer 1 begins to far exceed that of Oligo-C*. The maximum in the ET ratio corresponds to a near 1:1 ratio of polymer chains to Oligo-C*. At high polymer concentrations not every chain is as tightly complexed to Oligo-C* and the donor emission rises faster than that of the signaling chromophore. Such a relationship is expected, since when [polymer 1]/[Oligo-C*]<1, not all sensor polynucleotide strands can be complexed efficiently to independent polymer chains. Conversely, in the [polymer 1]/[Oligo-C*]>1 regime, not all the photons harnessed by polymer 1 (the donor) can be transferred to the Oligo-C* (the acceptor). Once the repeat unit of polymer to Oligo-C* reaches approximately 100, the photoluminescence of the reporting chromophore no longer increases, indicating acceptor saturation. Integrated fluorescence emission at this ratio was ~4 fold greater than that of the directly excited (480 nm) probe in the absence of polymer 1, giving further evidence of signal amplification.

Example 4

FRET Transfer from a Multichromophore Through a Sensor Polynucleotide to a Polynucleotide Dye for Improved Selectivity Hybridization of the Oligo-C* probe (5'-F1-ATCTTGACTATGTGGGTGCT-3') (SEQ ID NO: 4) leads to differences in the ET ratio to two different sensor chromophores. The sensor polynucleotide ([Oligo-C*]=$1\times10^{-8}$M) was annealed at 2° C. below its $T_m$ (58.5° C.) in the presence of an equal molar amount of a 20 base pair strand containing a complementary 20 base pair sequence, (5'-AGCACCCACATAGTCAAGAT-3') (SEQ ID NO: 5), and in an identical fashion with a non-complementary 20 base pair strand with the sequence (5'-CGTATCACTGGACTGATTGG-3') (SEQ ID NO: 6). The two DNA mixtures were mixed with Ethidium Bromide ([EB]=$1.1\times10^{-6}$M) at room temperature in potassium phosphate monobasic-sodium hydroxide buffer solution (50 mM, pH=7.40) where the intercalation of the EB occurred within the duplex structure of the hybridized DNA pair. Addition of polymer 1 in water ([1]=$1.6\times10^{-7}$M) and subsequent excitation of 1 (380 nm) resulted in energy transfer from 1 to the sensor polynucleotide and then energy transfer from the sensor polynucleotide to EB. Comparison of the resulting fluorescence reveals that the sensor solution only exhibited emission from the intercalating dye EB in the presence of the hybridized DNA. See FIG. 3. This result demonstrates that the DNA sequence sensor of this invention can detect the presence of target single stranded DNA with a specific base sequence complementary to that of the sensor polynucleotide by detecting the emission from a polynucleotide-specific dye upon excitation of a polycationic multichromophore. The chromophores used in this example were chosen for the proper overlaps in energy between the multichromophore and the two signaling chromophores.

Example 5

Demonstration of Optical Amplification of Polynucleotide Dyes Using FRET from Multichromophore Systems Excitation of 1 in a solution of 1, sensor polynucleotide and polynucleotide specific dye (Ethidium Bromide, EB) resulted in emission intensities of EB that were ~8 fold greater than that of the directly excited (500 nm) EB contained in the same double stranded DNA sequence which lacked the signaling chromophore on the sensor polynucleotide. Direct excitation of the signaling Oligo-C* (480 nm), in the absence of polymer 1, only provided an approximate 4 fold sensitization of the intercalated EB. Altogether, this example shows evidence of signal amplification by FRET from the polycationic multichromophore (conjugated polymer 1) to the diagnostic EB reporter. See FIG. 4.

Example 6

FRET Transfer to a Polynucleotide Dye

Figure 5:
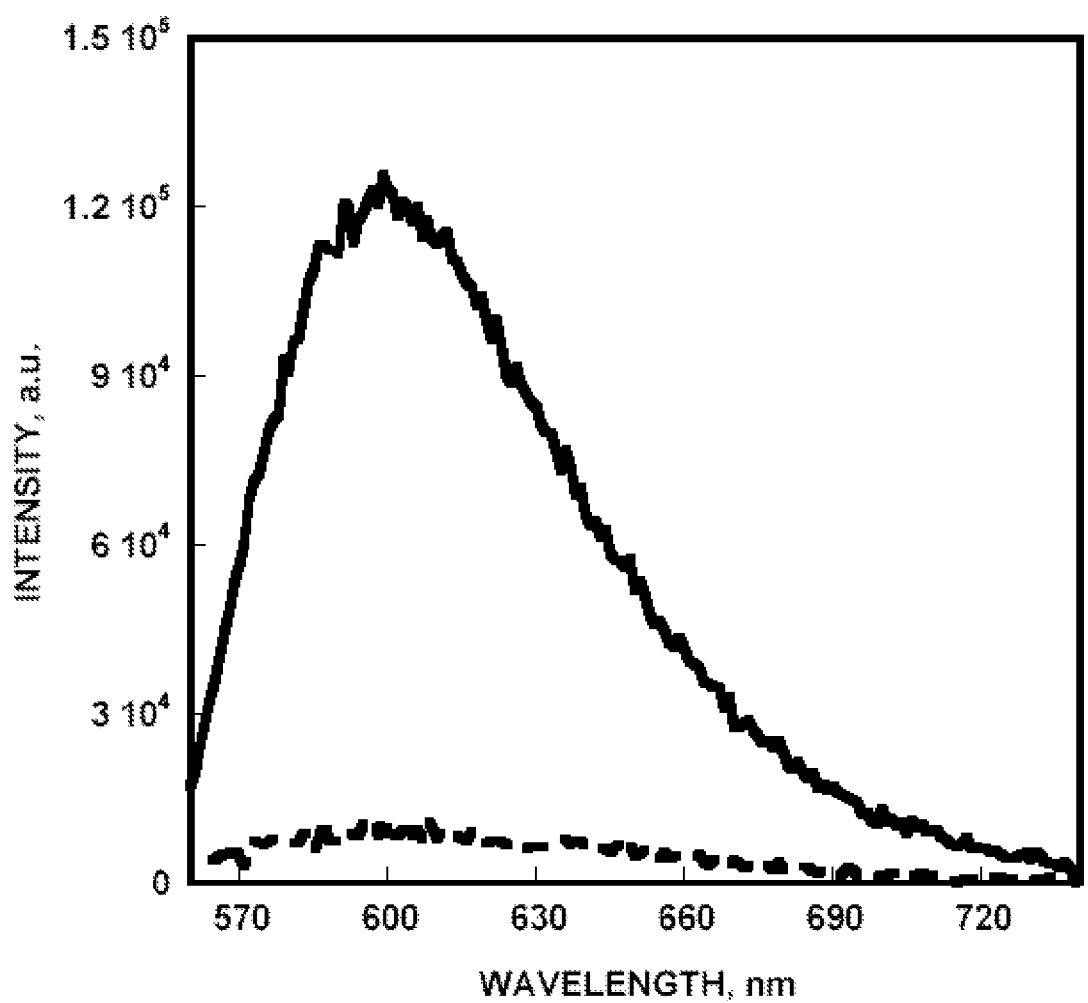
FIG. 5 presents the emission spectra of EB upon excitation of polymer 1 in the presence of EB and both hybridized (solid line) and non-hybridized (dotted line) sensor polynucleotides in potassium phosphate-sodium hydroxide buffer solution (50 mM, pH=7.40). See Example 6. The emission is a result of energy transfer from the polycationic multichromophore to the intercalated EB only in the case of the hybridized, double stranded DNA.

Experiments using 1 and ethidium bromide ("EB") as a signaling chromophore demonstrated that direct energy transfer from 1 to EB could be shown in the presence of double-stranded DNA. The sensor polynucleotide (5'-ATCT-TGACTATGTGGGTGCT-3') (SEQ ID NO: 4) lacking the signaling chromophore ([Oligo]=1×10$^{-8}$ M) was annealed at 2° C. below its $T_m$ (58.5° C.) in the presence of an equal molar amount of a 20 base pair strand containing a complementary 20 base pair sequence, (5'-AGCACCCACATAGTCAAGAT-3') (SEQ ID NO: 5), and in an identical fashion with a non-complementary 20 base pair strand with the sequence (5'-CGTATCACTGGACTGATTGG-3') (SEQ ID NO: 6). The two DNA mixtures were mixed with Ethidum Bromide ([EB]=1.1×10$^{-6}$ M) at room temperature in potassium phosphate monobasic-sodium hydroxide buffer solution (50 mM, pH=7.40) where the intercalation of the EB occurred within the duplex structure of the hybridized DNA pair. Addition of polymer 1 in water ([1]=1.6×10$^{-7}$ M) and subsequent excitation of 1 (380 nm) resulted in energy transfer from 1 to the intercalated EB only in the case of hybridized or double stranded DNA. Emission from the EB was detected upon excitation of polymer 1 for only the hybridized sequences. See FIG. 5.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

REFERENCES

[1] Wang, J. Nucleic Acid Res. 2000 28 3011.
[2] Umek, R. M.; Lin, S. W.; Vielmetter, J.; Terbrueggen, R. H.; Irvine, B.; Yu, C. J.; Kayyem, J. F.; Yowanto, H.; Blackburn, G. F.; Farkas, D. H.; Chen, Y. P. J. Mol. Diag. 2001 3 74.
[3] Schork N. J.; Fallin D.; Lanchbury J. S. Clini. Genet. 2000 58 250.
[4] Balakin, K. V.; Korshun, V. A.; Mikhalev, I. I.; Maleev, G. V.; Malakhov A. D.; Prokhorenko, I. A.; Berlin, Yu. A. Biosensors and Bioelectronics 1998 13 771.
[5] LePecg, J. B.; Paoletti, C. J. Mol. Biol. 1967 27 87.
[6] Petty, J. T.; Bordelon, J. A.; Robertson, M. E. J. Phys. Chem. B 2000 104 7221.
[7] Cardullo, R. A.; Agrawal, S.; Flores, C.; Zamechnik, P. C.; Wolf, D. E. Proc. Natl. Acad. Sci. 1988 85 8790.
[8] Castro, A.; Williams, J. G. K. Anal. Chem. 1997 69 3915.
[9] Knemeyer, J.; Marine, N.; Sauer, M. Anal. Chem. 2000 72 3717.
[10] Minehan, D. S.; Marx, D. A.; Tripathy, S. K. Macromolecules 1994 27 777.
[11] Pullman, B.; Layery, R.; Pullman, A. Eur. J. Biochem. 1982 124 229.
[12] McQuade, D. T.; Pullen. A. E.; Swager, T. M. Chem. Rev. 2000 100 2537.
[13] Chen, L.; McBranch, D. W.; Wang, H.-L.; Helgeson, R.; Wudl, F.; Whitten, D. G. Proc. Natl. Acad. Sci. U.S.A. 1999 96 12287.
[14] Dogariu, A., Gupta, R., Heeger, A. J., Wang, H. Synthetic Metals 1999 100 95.
[15] Kabanov, A. V.; Felgner, P.; Seymour, L. W., Eds. Self-Assembling Complexes for Gene Delivery. From Laboratory to Clinical Trial; John Wiley: Chichester, 1998.
[16] Kircheis, R.; Blessing, T.; Brunner, S.; Wightman, L.; Wagner, E. J. Controlled Release 2001 72 165.
[17] Wolfert, M. A.; Dash, P. R.; Navarova, O.; Oupicky, D.; Seymour, L. W.; Smart, S.; Strohalm, J.; Ulbrich, K. Bioconjugate Chem. 1999 10 993.
[18] Ganachaud, F.; Elaïssari, A.; Pichot, C.; Laayoun, A.; Cros, P. Langmuir 1997 13 701.
[19] Smith, J. O.; Olson, D. A.; Armitage, B. A. J. Am. Chem., Soc. 1999 121 2628.
[20] Harada, A.; Kataoka, K. Science 1999 283 65.
[21] Bronich, T. K.; Nguyen, H. K.; Eisenberg, A.; Kabanov, A. V. J. Am. Chem. Soc. 2000 122 8339.
[22] Stork, M. S.; Gaylord, B. S.; Heeger, A. J.; Bazan, G. C. Adv. Mater. 2002 14 361. The molecular weight of polymer 1 was determined to be 8,600 g/mole (Mn).
[23] Nielsen, P. E.; Egholm, M. Peptide Nucleic Acids: Protocols and Applications. Horizon Scientific Press, Portland, 1999.
[24] Makino, S.-I.; Uchida, I.; Terakado, N.; Sasakawa, C.; Yoshikawa, M.; J. Bacteriol. 1989, 171, 722.
[25] Lakowicz, J. R. Principles of Fluorescence Spectroscopy. Kluwer Academic/Plenum Publishers: New York, 1999.
[26] Wang, J.; Wang, D. L.; Miller, E. K.; Moses, D.; Bazan, G. C.; Heeger, A. J. Macromolecules 2000, 33, 5153.

What is claimed is:

1. A light harvesting multichromophore system, the system comprising
   a) a signaling chromophore; and
   b) a water-soluble conjugated polymer comprising a delocalized electronic structure, wherein the polymer can transfer energy from its excited state to the signaling chromophore to provide a greater than 4 fold increase in fluorescence emission from the signaling chromophore than can be achieved by direct excitation.

2. The light harvesting multichromophore system of claim 1, wherein the polymer can transfer energy from its excited state to a signaling chromophore to provide an 8 fold increase in fluorescence emission from the signaling chromophore than can be achieved by direct excitation.

3. The light harvesting multichromophore system of claim 1, wherein the signaling chromophore comprises a fluorescent dye.

4. The light harvesting multichromophore system of claim 1, wherein the conjugated polymer has the structure $$\left[ \underset{}{\underset{}{\bigcirc}}\text{—}\underset{R\ R}{\underset{}{\bigcirc\bigcirc}} \right]_n \quad 1$$

—R = —$(CH_2)_6 NME_3^{\oplus} I^{\ominus}$

5. The light harvesting multichromophore system of claim 1, wherein the system further comprises a substrate.

6. The light harvesting multichromophore system of claim 1, wherein the system further comprises a second signaling chromophore.

7. The light harvesting multichromophore system according to claim 6, wherein the second signaling chromophore comprises a fluorescent dye.

8. The light harvesting multichromophore system according to claim 6, wherein the second signaling chromophore is attached to a substrate.

9. The light harvesting multichromophore system according to claim 1, further comprises an excitation source.

10. The light harvesting multichromophore system according to claim 9, wherein the excitation source comprises a laser.

11. The light harvesting multichromophore system according to claim 1, wherein the system further comprises a detector.

12. The light harvesting multichromophore system according to claim 11, wherein the detector comprises a fluorometer.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Syhthetic oligonucleotide

<400> SEQUENCE: 1
gtaaatggtg ttagggttgc                                              20

<210> SEQ ID NO 2
<211> LENGTH: 40
<212> TYPE: DNA
```

```
<213> ORGANISM: Artificial Sequence
<220> FEATURE:
<223> OTHER INFORMATION: Synthetic oligonucleotide

<400> SEQUENCE: 2
catctgtaaa tccaagagta gcaaccctaa caccatttac                                40

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 3
aaaatattgt gtatcaaaat gtaaatggtg ttagggttgc                                40

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
atcttgacta tgtgggtgct                                                      20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
agcacccaca tagtcaagat                                                      20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
cgtatcactg gactgattgg                                                      20
```